US010959647B2

(12) United States Patent
Chang et al.

(10) Patent No.: US 10,959,647 B2
(45) Date of Patent: Mar. 30, 2021

(54) SYSTEM AND METHOD FOR SENSING AND RESPONDING TO FATIGUE DURING A PHYSICAL ACTIVITY

(71) Applicant: SEISMIC HOLDINGS, INC., Menlo Park, CA (US)

(72) Inventors: Andrew Robert Chang, Sunnyvale, CA (US); Andreas Martin Hauenstein, San Mateo, CA (US); Daniel Ly, Mountain View, CA (US); Ray Franklin Cowan, Mountain View, CA (US); Rebecca Shultz, Mountain View, CA (US)

(73) Assignee: SEISMIC HOLDINGS, INC., Menlo Park, CA (US)

(*) Notice: Subject to any disclaimer, the term of this patent is extended or adjusted under 35 U.S.C. 154(b) by 271 days.

(21) Appl. No.: 15/390,656

(22) Filed: Dec. 26, 2016

(65) Prior Publication Data
US 2017/0188894 A1 Jul. 6, 2017

Related U.S. Application Data

(60) Provisional application No. 62/273,425, filed on Dec. 30, 2015.

(51) Int. Cl.
A61B 5/11 (2006.01)
A61B 5/00 (2006.01)
(Continued)

(52) U.S. Cl.
CPC ............ A61B 5/1118 (2013.01); A61B 5/112 (2013.01); A61B 5/1121 (2013.01); A61B 5/486 (2013.01);
(Continued)

(58) Field of Classification Search
CPC .......... A61B 5/1116–1118; A61B 5/112–1128; A61B 5/7264; A61B 5/7267;
(Continued)

(56) References Cited

U.S. PATENT DOCUMENTS 4,633,094 A 12/1986 Knudsen
5,143,088 A 9/1992 Marras et al.
(Continued)

FOREIGN PATENT DOCUMENTS

WO 2011064705 A1 6/2011
WO 2011133799 A1 10/2011
(Continued)

OTHER PUBLICATIONS

Begg, R. "Computational intelligence for movement sciences: neural networks and other emerging techniques." IGI Global, 2006. pp. 2, 3, 57, 97, 152. (Year: 2006).*
(Continued)

Primary Examiner — David J. McCrosky
(74) Attorney, Agent, or Firm — Van Court & Aldridge LLP

(57) ABSTRACT

A system and method for utilizing an activity monitoring device that includes, during a set of initial activity sessions, collecting the kinematic data from an activity monitoring device and generating a temporal record of at least one biomechanical signal that is calculated from the kinematic data; analyzing temporal changes in the biomechanical signals during the initial activity sessions and characterizing a fatigue model; and, during a subsequent activity session collecting current kinematic data of a participant and generating at least one current biomechanical signal from the current kinematic data, monitoring the fatigue state through processing the at least one current biomechanical signal
(Continued)

according to the fatigue model, and triggering feedback in a user interface based on the fatigue state.

13 Claims, 20 Drawing Sheets

(51) Int. Cl.
    *G16H 50/30* (2018.01)
    *G16H 40/67* (2018.01)

(52) U.S. Cl.
    CPC ........... *A61B 5/7275* (2013.01); *G16H 40/67* (2018.01); *G16H 50/30* (2018.01); *A61B 2503/10* (2013.01); *A61B 2503/40* (2013.01); *A61B 2562/0219* (2013.01)

(58) Field of Classification Search
    CPC ... A61B 5/7271; A61B 5/7275; A61B 5/7282; A61B 2505/09
    See application file for complete search history.

(56) References Cited

U.S. PATENT DOCUMENTS

| | | | |
|---|---|---|---|
| 5,158,089 | A | 10/1992 | Swezey et al. |
| 5,388,591 | A | 2/1995 | Luca et al. |
| 5,398,697 | A | 3/1995 | Spielman |
| 5,749,838 | A | 5/1998 | Kline |
| 5,916,181 | A | 6/1999 | Socci et al. |
| 5,919,149 | A | 7/1999 | Knurl |
| 6,032,530 | A | 3/2000 | Hock |
| 7,264,554 | B2 | 9/2007 | Bentley |
| 7,431,703 | B2 | 10/2008 | Salvi et al. |
| 7,602,301 | B1 | 10/2009 | Stirling et al. |
| 7,634,379 | B2 | 12/2009 | Noble |
| 7,698,830 | B2 | 4/2010 | Townsend et al. |
| 8,206,325 | B1 | 6/2012 | Najafi et al. |
| 8,408,041 | B2 | 4/2013 | Ten Kate et al. |
| 8,749,391 | B2 | 6/2014 | Flinsenberg et al. |
| 8,773,256 | B2 | 7/2014 | Ten et al. |
| 8,924,248 | B2 | 12/2014 | Tropper et al. |
| 8,928,484 | B2 | 1/2015 | Chang et al. |
| 9,011,352 | B2 | 4/2015 | Ten Kate et al. |
| 9,128,521 | B2 | 9/2015 | Chang et al. |
| 9,286,782 | B2 | 3/2016 | Chang et al. |
| 2003/0050546 | A1 | 3/2003 | Desai et al. |
| 2003/0181832 | A1 | 9/2003 | Carnahan et al. |
| 2004/0015103 | A1 | 1/2004 | Aminian et al. |
| 2005/0126026 | A1 | 6/2005 | Townsend et al. |
| 2007/0015611 | A1 | 1/2007 | Noble et al. |
| 2007/0062279 | A1 | 3/2007 | Chan et al. |
| 2007/0115277 | A1 | 5/2007 | Wang et al. |
| 2007/0118056 | A1 | 5/2007 | Wang et al. |
| 2007/0167671 | A1 | 7/2007 | Miller |
| 2008/0288026 | A1 | 11/2008 | Cross et al. |
| 2008/0319352 | A1 | 12/2008 | Chow et al. |
| 2009/0069722 | A1 | 3/2009 | Flaction et al. |
| 2009/0076419 | A1 | 3/2009 | Namineni et al. |
| 2009/0312973 | A1 | 12/2009 | Hatlestad et al. |
| 2010/0152622 | A1 | 6/2010 | Teulings |
| 2010/0205541 | A1 | 8/2010 | Rapaport et al. |
| 2010/0211349 | A1 | 8/2010 | Flaction et al. |
| 2010/0298655 | A1 | 11/2010 | McCombie et al. |
| 2010/0312152 | A1 | 12/2010 | Sarkodie-Gyan et al. |
| 2010/0317489 | A1 | 12/2010 | Flaction |
| 2011/0063114 | A1 | 3/2011 | Ikoyan |
| 2011/0172951 | A1 | 7/2011 | Schlumbohm |
| 2011/0207581 | A1 | 8/2011 | Flaction |
| 2011/0264325 | A1 | 10/2011 | McLaughlin et al. |
| 2012/0016624 | A1 | 1/2012 | Caritu et al. |
| 2012/0053890 | A1 | 3/2012 | Acht et al. |
| 2012/0116550 | A1* | 5/2012 | Hoffman ................ G16H 40/67 |
| | | | 700/91 |
| 2013/0015976 | A1 | 1/2013 | Chang et al. |
| 2013/0084805 | A1 | 4/2013 | Pasquero et al. |
| 2013/0123669 | A1* | 5/2013 | Kinoshita ............... A61B 5/112 |
| | | | 600/595 |
| 2013/0158365 | A1 | 6/2013 | Chey et al. |
| 2013/0190657 | A1 | 7/2013 | Flaction et al. |
| 2013/0190658 | A1 | 7/2013 | Flaction et al. |
| 2013/0207889 | A1 | 8/2013 | Chang et al. |
| 2014/0228985 | A1 | 8/2014 | Elliott et al. |
| 2014/0244009 | A1 | 8/2014 | Mestas et al. |
| 2014/0270387 | A1 | 9/2014 | Hoof et al. |
| 2014/0277633 | A1 | 9/2014 | Flaction |
| 2014/0364769 | A1 | 12/2014 | Chang et al. |
| 2015/0040669 | A1 | 2/2015 | Borkholder et al. |
| 2015/0100141 | A1 | 4/2015 | Hughes |
| 2015/0118669 | A1* | 4/2015 | Wisbey ............... G06F 19/3481 |
| | | | 434/247 |
| 2015/0228118 | A1 | 8/2015 | Eade et al. |
| 2016/0014826 | A1 | 1/2016 | Mizikovsky et al. |
| 2016/0042529 | A1 | 2/2016 | Tao et al. |
| 2016/0051858 | A1 | 2/2016 | Flaction et al. |
| 2016/0128619 | A1 | 5/2016 | Geller et al. |
| 2017/0049335 | A1* | 2/2017 | Duddy ................. A61B 5/0205 |
| 2017/0095181 | A1 | 4/2017 | Hauenstein et al. |
| 2017/0095692 | A1 | 4/2017 | Chang et al. |
| 2017/0095693 | A1 | 4/2017 | Chang et al. |
| 2017/0182360 | A1 | 6/2017 | Chang et al. |
| 2017/0188894 | A1 | 7/2017 | Chang et al. |
| 2017/0189752 | A1* | 7/2017 | Mohrman ............ A61B 5/7271 |
| 2017/0258374 | A1 | 9/2017 | Ly et al. |
| 2017/0273601 | A1 | 9/2017 | Wang et al. |
| 2017/0344919 | A1 | 11/2017 | Chang et al. |

FOREIGN PATENT DOCUMENTS

| | | |
|---|---|---|
| WO | 2013024461 A1 | 2/2013 |
| WO | 2015069124 A1 | 5/2015 |

OTHER PUBLICATIONS

Clifford, Michelle and Gomez, Leticia (2005), "Measuring Tilt with Low-g Accelerometers", in Freescale Semiconductor Application Note, (accessible at http://wvvw.freescale.com/files/sensors/doc/app_note/AN3107.pdf), pp. 01-8.

Kesson, Malcolm (2002), "Mel. Align Y Axis to Vector", in CG References & Tutorials at Fundza.com (accessible at http://www.fundza.com/mel/axis_to_vector/align_axis_to_vector.html), pp. 1-6.

Patel, A.T. and Ogle, Abna A. (2000), "Diagnosis and Management of Acute Low Back Pain", in American Family Physician 15:61 (6) (accessible at http://aafp.org/afp/2000/0315/p1779.html), pp. 1779-1786.

Unknown (2000), "Information from Your Family Doctor Acule Low Back Pain", in American Family Physician 15 51(6} (accessible at http://www.aafp.org/afp/2000/0315/p1789 html), pp. 1-4.

Unknown, "Accelerometer", in Wikipedia (archived Apr. 1, 2011 at http:i/web archive.org/V\leb/2011 0401205940/http://en.wikipedia.org/wiki/Accelerometer), pp. 1-21.

Unknown, "Back Pain", in Wikipedia (archived Feb. 25, 2011 at http:I/web.archive.org/web/20110225132'125/ 0http://en.wikipedia.orgiwiki/Back~pain) . . . pp. 1-22.

Unknown, "Mahalanobis Distance", in Wikipedia (ardlived Mar. 29, 2010 at http://web.archive.orf!/ 0 webi20100329232341/http:/len.wikipedia.org.l'<>viki/Mahalanobis_distance), pp. 1-8.

Unknown, "Rotation", in Wikipedia (archived I'vlarch 31, 2011 at http://web archive.org/web/20110331232736/http://en.wikipedia.org/wiki/Rotation), pp. 1-13.

Unknown, "A Patient's Guide to Rehabilitation for Low Back Pain", University of Maryland Spine Program (archived Jun. 8, 2011 at http://web.archive.org/web/20110607181952/http://www.umm.edu/spinecenter/education/rehabilitation_for_low_back_pain.htm). pp. 1-10.

Unknown, "Sensors", at freescale.com (accessed May 14, 2012 at http://www.freescale.com/webapp/sps/site/homepage.jsp?nodel=011269). pp. 1-2.

(56) References Cited

OTHER PUBLICATIONS

Unknown, "Neutral Spine", in Wikipedia (archived Feb. 12. 2011 at http://web.archive.org/web/20110212145135/http://en.wikipedia.orglwiki/Neutral_spine), pp. 1-7.

\* cited by examiner

Training Recommendations

| Stage | Description | Time Condition | Fatigue Condition |
|---|---|---|---|
| 1 | Warm up | 3:00 | - |
| 2 | Easy Sprint | - | >50 |
| 3 | Recover | - | <25 |
| 4 | Easy Sprint | - | >50 |
| 5 | Recover | - | <25 |
| 6 | Moderate Sprint | - | >75 |
| 7 | Recover | - | <25 |
| 8 | Hard Sprint | - | >100 |
| 9 | Recover | - | <25 |
| 10 | Very Hard Sprint | - | >125 |
| 11 | Cool Down | 5:00 | <25 |

SYSTEM AND METHOD FOR SENSING AND RESPONDING TO FATIGUE DURING A PHYSICAL ACTIVITY

CROSS-REFERENCE TO RELATED APPLICATIONS

This Application claims the benefit of U.S. Provisional Application No. 62/273,425, filed on 30 Dec. 2015, which was incorporated in its entirety by this reference.

TECHNICAL FIELD

This invention relates generally to the field of activity monitoring, and more specifically to a new and useful system and method for sensing and responding to fatigue during a physical activity.

BACKGROUND

It is currently very complicated to analyze the state of fatigue in an athlete such as a runner. The lactate concentration in blood is one signal that can be used to identify when a participant enters a state of fatigue. The lactate threshold can be a useful measure for defining exercise intensity for training and racing in endurance sports. However, the lactate threshold is different between different individuals and can change with the fitness level of the individual. Measuring blood lactate concentrations is often performed in a testing environment and is performed by taking blood samples when exercising. Thus, such fatigue detection is prohibitive to non-test subject scenarios and even then, it is mostly limited to treadmill activities. Thus, there is a need in the activity monitoring field to create a new and useful system and method for sensing and responding to fatigue during a physical activity. This invention provides such a new and useful system and method.

DESCRIPTION OF THE EMBODIMENTS

The following description of the embodiments of the invention is not intended to limit the invention to these embodiments but rather to enable a person skilled in the art to make and use this invention.

1. Overview

A system and method for sensing and responding to fatigue during a physical activity of a preferred embodiment functions to utilize a change in biomechanical signals as an indicator of fatigue. The system and method preferably uses the motion of a participant as they perform an action to determine if the participant is fatigued. The kinematic motion can be characterized as biomechanical signals. The biomechanical signals are preferably for repeated actions such as the exemplary running biomechanical signals of motion paths, ground contact time, cadence, braking, pelvic rotation, pelvic tilt, pelvic drop, vertical oscillation of the pelvis, forward oscillation, forward velocity properties of the pelvis, step duration, stride or step length, step impact or shock, foot pronation, body loading ratio, foot lift, and/or other signals. Herein, use of ground contact time and kinematic motion path are used as the primary examples in detecting fatigue, but any additional or alternative biomechanical signals can be used.

Figure 2:
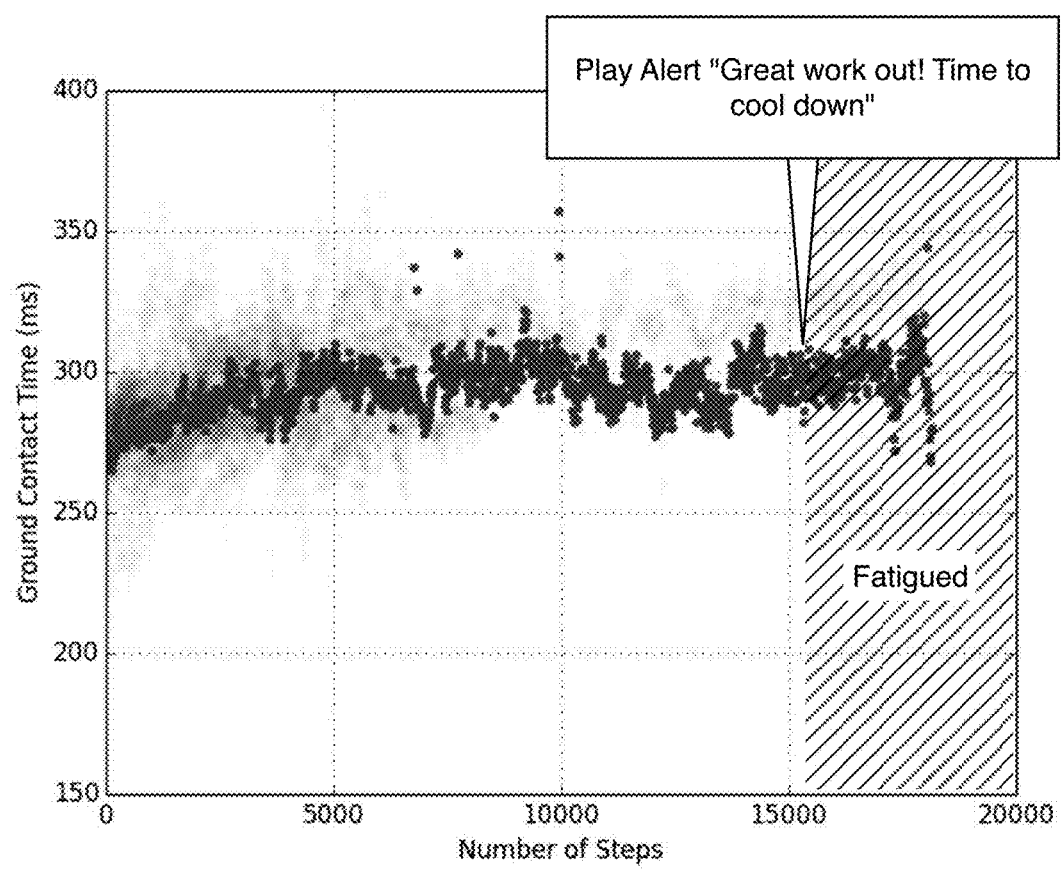
FIG. 2 is a graph representation of ground contact time during a run where the runner became fatigued.

As discovered by the inventors, ground contact time and/or body motions patterns for a routine action go through a significant change once fatigue sets in. In a first example, the ground contact time signal of a runner may trend upwards over the course of a run. The base value and/or the variance value will remain within some range when not fatigued, but the base value and/or variance value of the ground contact time may increase above a threshold when in a fatigued state as shown in FIG. 2.

Figure 3:
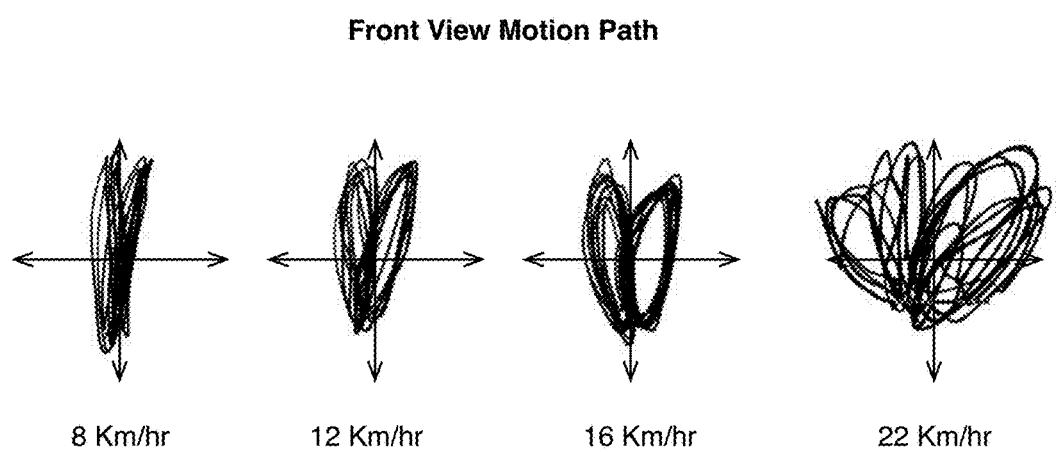
FIG. 3 is a schematic representation of transitions in a motion path during different intensities of an activity.
Figure 4:
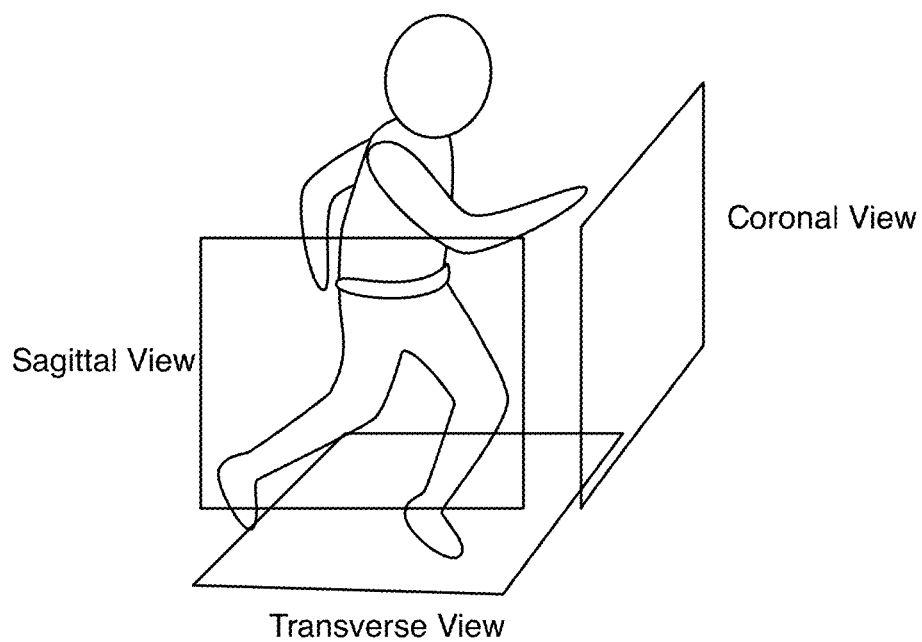
FIG. 4 is a schematic representation of different planes of motion paths.

In another example the two or three-dimensional motion path of a leg during each stride will generally follow a consistent pattern when running within the comfort zone of that participant. As the participant becomes fatigued or the intensity of the exercise increases, the pattern may become erratic and/or change form as shown in FIG. 3. For example, a runner may suddenly start running with a stronger bias for one leg and with less consistency between strides. Quantitatively, the "composure" or balance of the running motion is lost when fatigue sets in for a participant. Additionally, at some intensity threshold, a non-linear transition for the kinematic motion patterns may occur, which may be used in identifying a fatigue and/or potential injury threshold. The kinematic motion paths can be one, two, or three dimensional position traces over time. In one preferred implementation, the two-dimensional motion path in the sagittal plane, coronal plane, and transverse plane can be used as the monitored references as shown in FIG. 4.

When performing a repetitive action, such as taking a running stride, the pattern of motion will vary depending on the intensity, duration of activity, the participant, and/or other factors. When operating within a comfortable intensity level, the biomechanical signals may have a consistent profile that exhibit steady values, change in intensity, and/or changes with time. Changes may be characterized by different traits such as linear changes or other change trends. The patterns of biomechanical signals will generally change when the intensity changes, the participant grows tired, the participant incurs an injury, as the duration of the activity is prolonged, or other suitable changes occur. A set of biomechanical signals can be monitored for consistency and variance in detecting changes.

A biomechanical signal preferably parameterizes a biomechanical-based property of some action by a user. More particularly, a biomechanical signal quantifies at least one aspect of motion that occurs once or repeatedly during a task. For example, in the case of walking or running, how a participant takes each step can be broken into several biomechanical signals. In a preferred implementation, the system and method preferably operate with a set of biomechanical signals that can include ground contact time, braking, pelvic rotation, pelvic tilt, pelvic drop, vertical oscillation of the pelvis, forward oscillation, forward velocity properties of the pelvis, step duration, stride or step length, step impact or shock, and/or foot pronation. Additionally, the biomechanical signals can include left/right foot detection, which may be applied for further categorizing or segmenting of biomechanical signals according to the current step side. The pelvis is used as a preferred reference point for a wide variety of activities, including running. The pelvis can have a strong correlation to lower body movements and can be more isolated from upper body movements such as turning of the head and swinging of the arms.

The set of biomechanical signals may form a primitive set of signals from which a wide variety of activities can be monitored and analyzed. Herein, the system and method is particularly applied to running, but the method can additionally or alternatively be applied to other physical activities. For example, the system and method may be applied to activity use-cases such as gait-analysis, walking, running, lifting, swimming, skiing, skating, biking, rowing, golfing, baseball, basketball, bowling, soccer, football, dancing/choreography, ballet and/or any suitable activity. The activity is preferably characterized by predictable, repetitive, or predefined movements. The system method can be applied to helping a participant improve performance, track progress, and/or avoid injury in the sporting field, but can similarly be applied to physical rehabilitation and other clinical applications. Herein, fatigue is used as the qualitative description but such a measure can reasonably be taken as a composure level, comfort level, consistency level, and/or a level of risk for injury.

In one preferred use case, the system and method can be used in detecting when a participant reaches a critical fatigue state. The fatigue state may be indicative of accomplishing some exercise or fitness goal. Additionally or alternatively, the system and method can be used in detecting the onset of potential injury. The system could be used in detecting performance and biomechanical changes that are signs of or early warning indicators of an injury, measuring recovery from injury and/or preventing injury. Exemplary use cases relating to injury detection can identify high-risk states, identifying a type of injury, and measuring recovery progress from an injury.

Additionally, the system and method herein are primarily described as being used with a human participant, but the system and method could alternatively be used with other types of animals such as a dog, a horse, and the like. For example, the running biomechanical signals of horses could be analyzed and used to detect when the horse becomes fatigued or to warn of potential injury.

2. System

Figure 1:
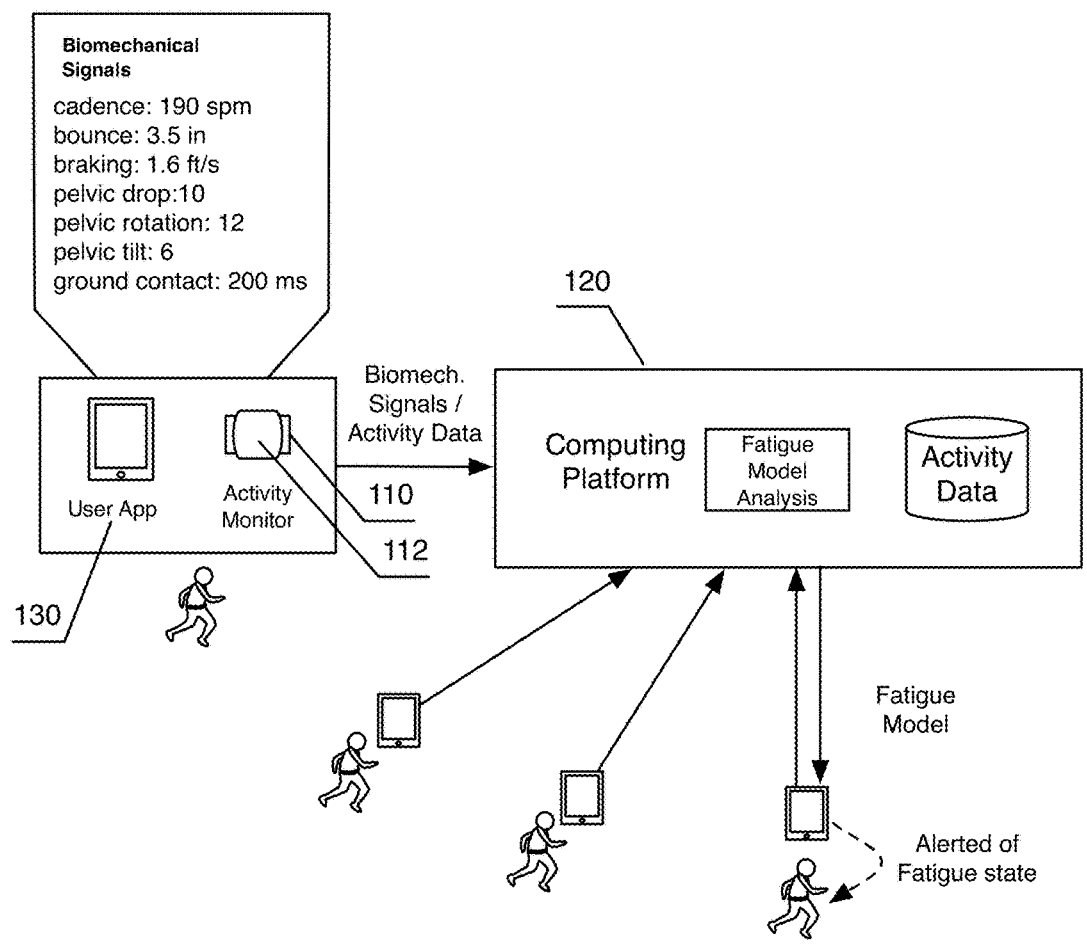
FIG. 1 is a schematic representation of a system of a preferred embodiment.

As shown in FIG. 1, a system for sensing and responding to fatigue during a physical activity of a preferred embodiment includes an activity monitoring device 110 and optionally a computing platform 120, and/or a secondary computing device 130 in communication with the activity monitoring device 110. The system functions to monitor movements of a participant during an activity for indications of fatigue. The components of the system function to cooperatively perform the methods of fatigue monitoring and detection described herein. In a preferred implementation, the activity monitoring device 110 uses wireless communication (e.g., Bluetooth) to connect to the secondary computing device 130, and the secondary computing device communicates with the computing platform 120 for synchronizing data and/or fatigue detection configuration. Alternative implementations implement the method with the activity monitoring device 110 in communication directly with user feedback elements such as tactile feedback elements, an audio system, or a display. The system can be configured for various activities. Herein, the system is described as it could be applied to running but is not limited to running.

The activity monitoring device 110 functions as a motion sensing device coupled to some point affected by the action of a participant. The activity monitoring device 110 preferably includes an inertial measurement system 112 and a housing compartment. The activity monitoring device 110 can additionally include any suitable components to support computational operation such as a processor, RAM, Flash memory, battery, user input elements (e.g., buttons, switches, capacitive sensors, touch screens, and the like), user output elements (e.g., status indicator lights, graphical display, speaker, audio jack, vibrational motor, and the like), a communication module or components (e.g., Bluetooth LE, Zigbee, NFC, Wi-Fi, and the like), and/or other suitable components. The activity monitoring device 110 is preferably small enough to be mounted to a participant in an unobtrusive way and may be integrated into a wearable such as a belt, a bracelet, a watch, clothing, shoes, or other articles. In alternative embodiments the activity monitoring device 110 may be a multipurpose wearable computing device such as a smart phone, a smart watch, smart glasses, or any suitable computing device.

The inertial measurement system 112 of the activity monitoring device 110 functions to measure multiple kinematic properties of an activity. The inertial measurement system 112 preferably includes at least one inertial measurement unit (IMU). An IMU can include at least one accelerometer, gyroscope, magnetometer, or other suitable inertial sensor. The IMU preferably includes a set of sensors aligned for detection of kinematic properties along three perpendicular axes. In one variation, the inertial measurement unit is a 9-axis motion-tracking device that includes a 3-axis gyroscope, a 3-axis accelerometer, and optionally a 3-axis magnetometer. The device may also include GPS, pulse oximeter, galvanic skin response and an altimeter sensor. The inertial measurement system 112 can additionally include an integrated processor that, among other functionality, provides sensor fusion, which effectively provides a separation of forces caused by gravity from forces caused by speed changes on the sensor. The integrated processor may additionally provide post processing of kinematic data.

Preferably kinematic data can be processed into biomechanical signals. The on-device sensor fusion may provide other suitable sensor conveniences or sensor data processing.

In one embodiment, the activity monitoring device 110 measures kinematic data at a single location. In an alternative embodiment, the activity monitoring device 110 comprises multiple inertial measurement systems 112 coupled, attached, or otherwise positioned at different locations. An inertial measurement system 112 can be coupled to a point on the participant's body. For example, a set of inertial measurement systems 112 can be positioned at the waist region, the shank of one or two legs, one or two feet, the thigh of one or two legs, the upper body, the upper arm, the lower arm, the head, or any suitable position on the body. Alternatively, an inertial measurement system 112 can be coupled to a point on a piece of equipment used during the activity such as a golf club, a bike wheel or pedal, a rowing oar, a basketball, a baseball, a baseball bat, a weight lifting bar, a tennis racket, or any suitable piece of equipment. For example one or more inertial measurement system(s) 112 and their associated components (e.g., power source, housing, and communication modules) can be attached to a handle or head of a golf club. The location or positioning of an activity monitoring device 110 and a set of inertial measurement systems 112 may depend on the activity.

In other variations, the activity monitoring device 110 can include an inertial measurement system 112 or other suitable sensing elements within the environment of the activity. For example, a treadmill could include an inertial measurement system 112 integrated into a running platform of the treadmill. In one implementation, a treadmill can be designed to detect and respond to fatigue in a runner.

The kinematic data is preferably sensed by the IMU and then transformed into biomechanical signals on a processor of the activity monitoring device. Alternatively, part or all of the generation of biomechanical signals may be generated by a processor outside of the activity monitoring device 110 such as a processor of the computing platform 120 or the secondary computing device 130. The activity monitoring device 110 can additionally include other sensors such as an altimeter, GPS, magnetometer, or any suitable sensor.

The computing platform 120 functions to collect and process data from a plurality of users. Collection of data from a plurality of participants can enable dynamic and continued refinement of fatigue detection and the corresponding fatigue models. The computing platform 120 may be used to serve a variety of types of activities. Alternatively, the computing platform 120 may be designed around a single type of activity such as running.

A secondary computing device 130 functions to be a supporting device to an activity monitoring device 110. The secondary computing device may provide processing capabilities, user interface capabilities (e.g., touch input, audio systems, a display, tactile feedback elements, and the like), sensing capabilities, communication capabilities, and/or other features that may not be provided in the activity monitoring device 110. In one preferred implementation, the activity monitoring device 110 communicates locally to the secondary computing device 130. The secondary computing device 130 can be a smart phone, a smart watch, a tablet, or any suitable computing device. Data from the activity monitoring device 110 can be communicated to the computing platform 120 through the secondary computing device as shown in FIG. 1. For example, a secondary computing device 130 may collect activity contextual data like GPS information and weather information during an activity session. In alternative embodiments, the activity monitoring device 110 may include communication components to communicate with the computing platform without dependence on a secondary computing device 130. The secondary computing device 130 preferably executes a user application, though a user application may alternatively be managed by the activity monitoring device 110 and/or the computing platform 120.

The user application functions to provide activity tracking and user feedback in cooperation with the activity monitoring device 110. The user application is preferably in communication with the activity monitoring device 110, however the activity monitoring device 110 may not need to be connected to the user application to analyze fatigue and provide feedback. The user application and the activity monitoring device 110 preferably communicate over Bluetooth LE but any suitable communication protocol or medium may be used. The activity monitoring device 110 preferably communicates data relating to the kinematic activity. Preferably, the kinematic activity data from an IMU of the activity monitor is transferred to the user application.

The user application can be any suitable type of user interface component. Preferably, the user application is a graphical user interface operable on a user computing device. The user computing device can be a smart phone, a tablet, a desktop computer, a TV based computing device, a wearable computing device (e.g., a watch, glasses, etc.), or any suitable computing device. The user application may facilitate part or all of signal processing. Portions of the signal processing may alternatively be implemented on the activity monitoring device 110 or in the computing platform 120.

Various forms of feedback can be delivered and/or controlled by the user application. For example, the detection of fatigue may be applied to notifying a participant of information relating to fatigue, analyzing performance and fatigue in one or more sessions, and guiding a participant when training or performing. Feedback could be in the form of audio cues (e.g., sounds and/or spoken audio), visual representation of information on a screen, haptic feedback, and/or other forms of feedback.

A processor system can be configured to facilitate monitoring and detecting of fatigue for a user of the activity monitoring device 110. A processor system preferably includes multiple processors: a processor at the activity monitoring device 110, a processor at the computing platform 120, and/or a processor at the secondary computing device 130. Alternatively, a single processor may be singularly responsible for monitoring and detecting fatigue. In one implementation, the system can be configured to provide user feedback when the biomechanical signals of a participant indicate fatigue. In another implementation, training recommendations may be generated and presented so as to target different fatigue objectives. For example, interval training could be used to transition a runner between non-fatigued state and a fatigue state multiple times until the level of fatigue indicates the activity session should conclude. In another implementation, the system could generate running route options based on a predicted onset of fatigue. For example, a user application could direct a runner where to run so as to satisfy a healthy level of fatigue during a running session. In another example, a graphical map could show where the onset of fatigue is predicted based on the runner's current state and location. The system and its capabilities to detect and respond to fatigue may alternatively be used for other suitable use cases.

3. Method

Figure 5:
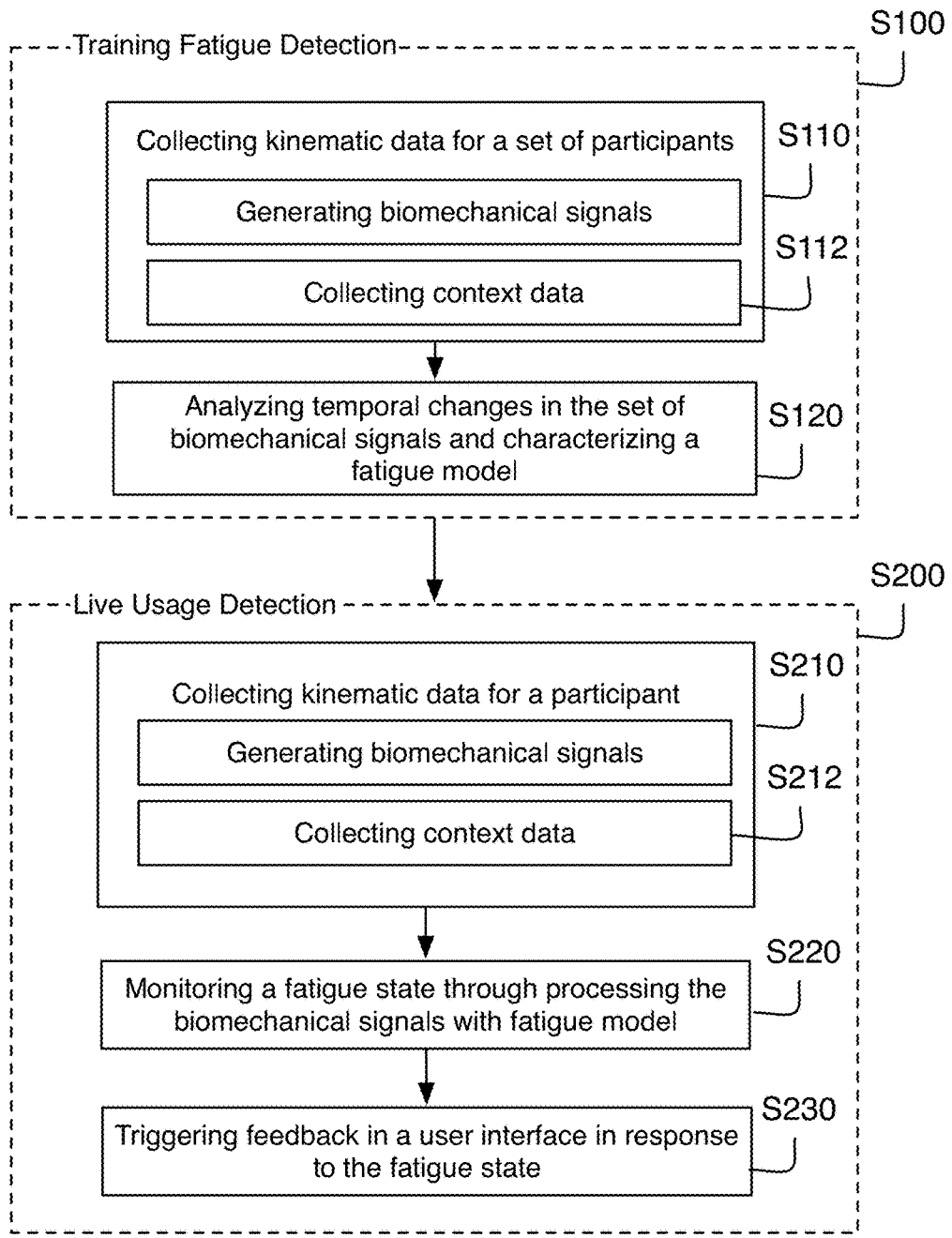
FIG. 5 is a flowchart representation of a method of a preferred embodiment.

As shown in FIG. 5, a method for sensing and responding to fatigue during a physical activity of a preferred embodiment includes establishing a fatigue model based on at least one biomechanical signal of a participant S100, collecting kinematic data and generating at least one biomechanical signal S210, monitoring fatigue state through processing the at least one current biomechanical signal according to the fatigue model S220, and triggering feedback in a user interface in response to a fatigue state S230. Establishing a fatigue model preferably includes collecting kinematic data and generating a set of biomechanical signals S110 and analyzing temporal changes in the set of biomechanical signals and characterizing the fatigue model S120.

Figure 6:
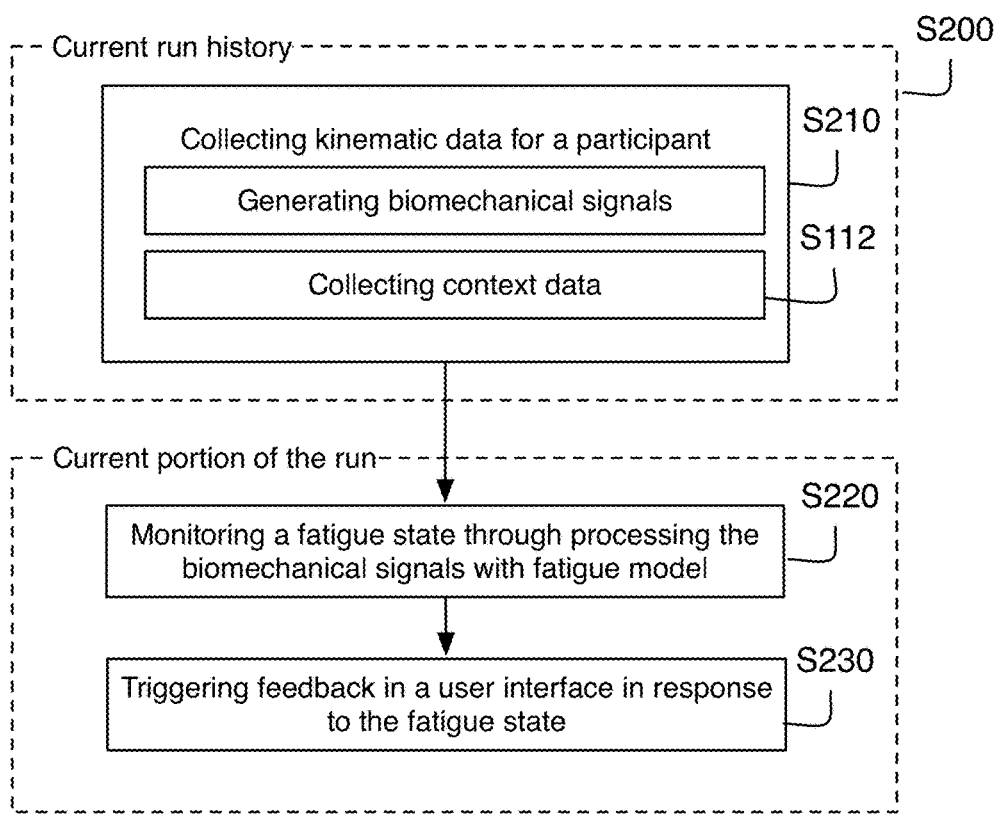
FIG. 6 is a flowchart representation of a variation of a method of a preferred embodiment using offline machine learning or predefined fatigue models.

The method functions to identify a fatigue state and/or a measure fatigue during one or more activity sessions and then perform some transformative action in response to such detection. The fatigue state is determined using a fatigue model, which can be set of conditions, threshold values, algorithmic processing configurations (e.g., neural net settings), and/or other properties used in specifying how fatigue or levels of fatigue may be detected. The method preferably utilizes kinematic measurements from an activity monitoring device. Such an activity monitoring device can preferably be worn unobtrusively. Furthermore, the method can enable fatigue detection to be customized to an individual. The characterization and detection can be dynamically adjusted to account for the biomechanical properties of a participant which may be influenced by fitness level, body type, performance tendencies (e.g., the type of runner). In one implementation, establishing a fatigue model S100 is performed for a particular participant to develop a personalized fatigue model. Alternatively or additionally, a generalized, predefined fatigue model may be set such that fatigue may be monitored without individualized calibration as shown in FIG. 6. Accordingly, a method of detecting fatigue state during an activity session S200 can be performed independently from establishing a fatigue model based on at least one biomechanical signal of a participant S100.

In a first variation, the method can use a machine intelligence approach. A machine intelligence approach preferably trains detection of fatigue on data from a participant. The trained fatigue detection could then be applied to detect fatigue on the same participant. Alternatively, machine intelligences may be performed on a set of participants, and the results of the training can be applied to one or more participants who may or may not have been part of the training set. In some cases, the data used to train the machine intelligence is collected with particular conditions so as to be most applicable to a set of target audiences.

A second variation of the method can use a heuristic-based approach. The heuristic-based approach may have a set of heuristics that are used in identifying fatigue in changes of biomechanical signals. The heuristics could be algorithmic and rule-based approaches to detecting events, patterns, and/or other conditions associated with a fatigue model.

A third variation of the method can use a hybrid approach, which uses machine intelligence in combination with heuristics. For example, the heuristic approach may be used initially but machine intelligence can gradually learn the normal performance tendencies of an individual and adjust use of the heuristics.

Block S100, which includes establishing a fatigue model based on at least one biomechanical signal of a participant, functions to set an approach to detecting fatigue from data collected from an activity monitoring device. Block S100 may be an optional process within the method, and the method may alternatively be implemented wherein the characterization of a fatigue model is preset or otherwise determined. In general, establishing a fatigue model preferably includes one or more initial sessions of activity of analyzing one or more participants. Block S100 can include collecting kinematic data and generating a set of biomechanical signals S110 and analyzing temporal changes in the set of biomechanical signals and characterizing a fatigue model S120.

Block S110, which includes collecting kinematic data and generating a set of biomechanical signals, functions to obtain motion data of a participant used to analyze fatigue. Block S110 is preferably substantially similar to Block S210 wherein kinematic data is collected and transformed into biomechanical signals. In some cases, the collected kinematic data and generated biomechanical signals can be used in establishing or updating a fatigue model and in applying fatigue detection to a current activity session.

Figure 7:
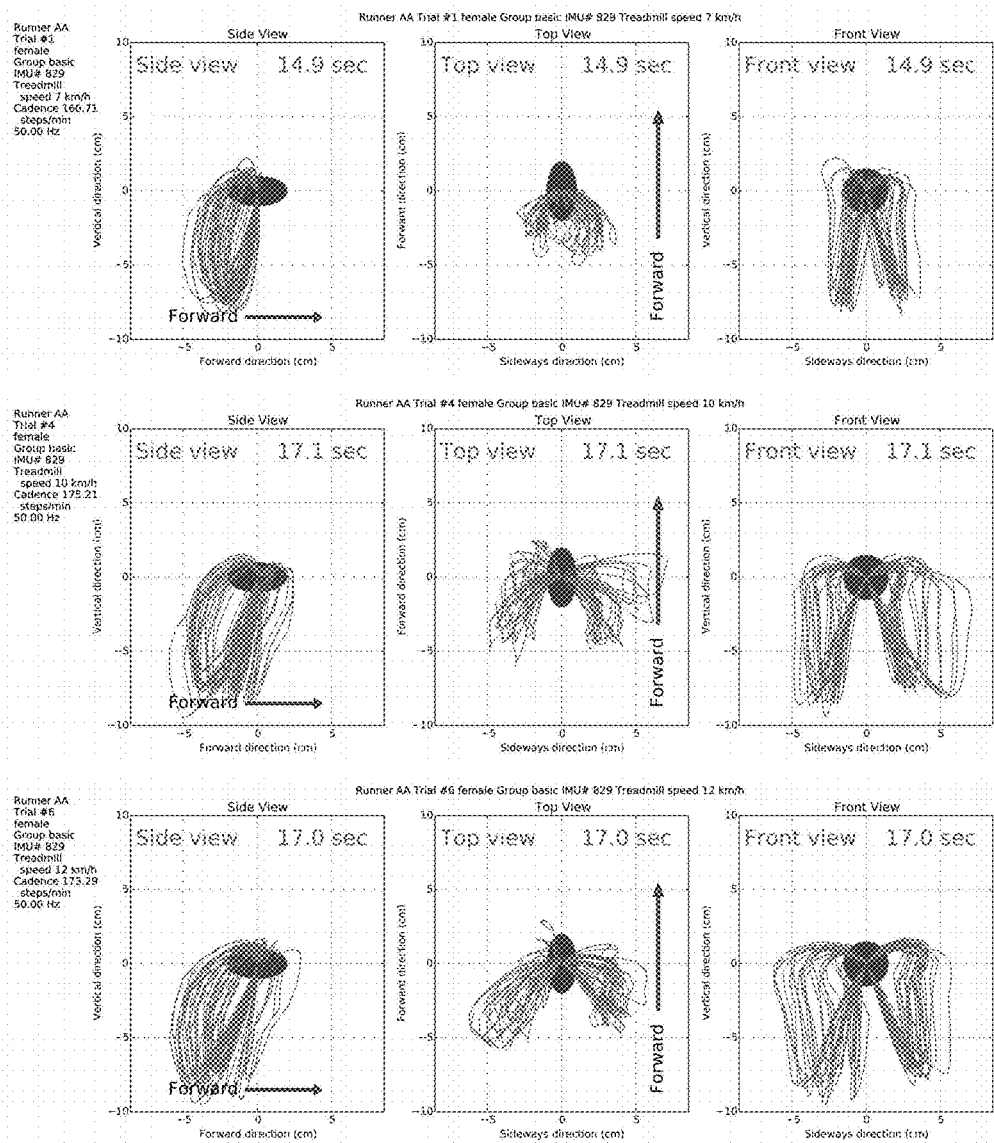
FIGS. 7 and 8 are exemplary motion path representations for various contexts.
Figure 8:
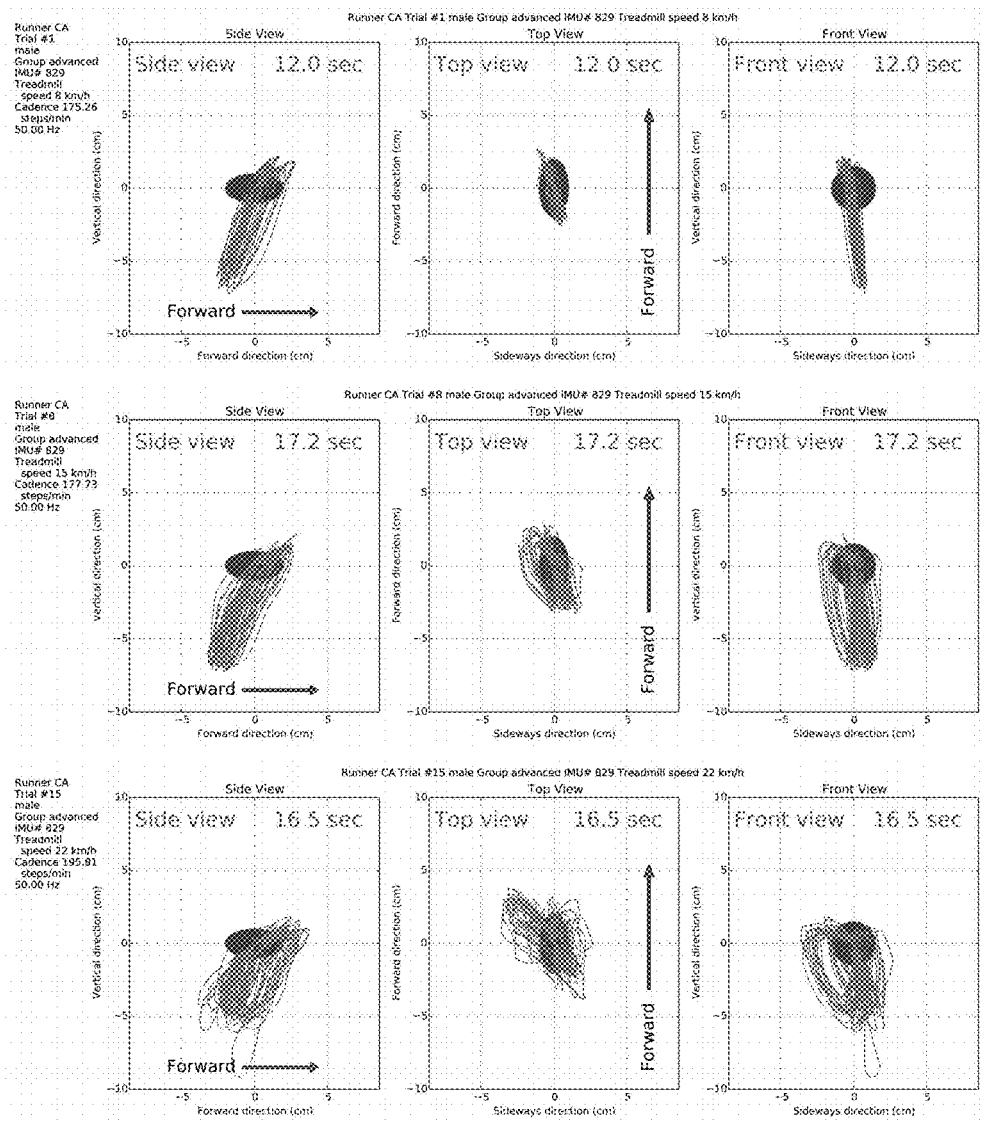

Biomechanical signals can be collected under different conditions such as different activity intensities (e.g., running speed), at different points during the activity (e.g., beginning, middle, end), and/or optionally at different contextual conditions. Collecting at different contextual conditions may include collecting data for different terrain types, weather conditions, hilly paths vs. flat paths, and/or other conditions. The collection of activity data for use in characterizing a pattern of fatigue can be performed prior to using the patterns of fatigue for identifying fatigue during live conditions Data collection can be performed for an individual user, a set of controlled user or users, and/or for a set of uncontrolled users. In the individual user variation, the method can build very individualized information for the present participant. Not everyone will exhibit identical running form, and thus, motion paths for an activity will generally vary between participants. For example, the motion paths of the male and female runner in FIGS. 7 and 8 have different motion path patterns. Additionally, motion paths can have different patterns within an individual for a fatigued state and a non-fatigued state as exemplified between the top row of motion paths (e.g., low level of exertion) and the bottom row of motion paths (e.g., high level of exertion) in FIGS. 7 and 8. Individualized information can help train fatigue detection for the individual. Additionally, the method may include guiding an individual through training data collection, which functions to facilitate collecting data in a variety of scenarios. For example, during an initial training period, audio instructions could instruct a user to run faster or slower over some running session so that motion path information and/or other information can be collected. The guiding of the individual could be predefined but can additionally be dynamic. For example, if biomechanical signal data is not yet collected for running up a steep incline, and it is detected that the participant is currently running up a hill, the audio instructions can direct a participant to run in a comfortable state and then to run at faster rates to characterize biomechanical signal data on an incline over a variety of intensifies.

In the controlled users variation, the patterns of fatigue can be measured and identified through participants included in a controlled study. For example, a base set of data can be characterized for a set of participants with different demographics and activity experience, and the data can be collected in controlled environments. For example, the fatigue properties for a novice runner could be characterized in the same conditions as an expert runner. Data from the controlled users can be a useful way of setting or seeding initial training data, which would include capturing heart rate or blood lactic acid data to identify when users are indeed fatiguing.

In the variation of using a set of uncontrolled users, data from numerous participants can be used in combination. A platform with access to biomechanical signal data for a large number of users may be able to leverage access to this data to improve fatigue detection. Machine learning or other suitable algorithmic approaches can be used to identify patterns in block S120.

Block S110 and/or S210 can be implemented with a single point activity monitoring device. The activity monitoring device is preferably a sensing device with at least one inertial measurement unit (e.g., an accelerometer and/or gyroscope), but any suitable sensing system may be used. The activity monitoring device is preferably positioned in the waist region, and more specifically, the activity monitoring device can be positioned along the back in the lumbar or sacral region. In another variation, the activity monitoring device uses a multi-point sensing approach wherein a set of inertial measurement systems measure motion at multiple points. In a running context, the points of measurement may be in the waist region, the upper leg, the lower leg, and/or the foot. Other points of measurement can include the upper body, the head, or portions of the arms. In alternative activity applications, equipment such as a golf club, a tennis racket, or other activity items can have attached activity monitoring devices. The activity monitoring device may alternatively use any alternative approach to sensing collecting kinematic data.

In one implementation, the biomechanical signal generation can use various approaches to converting kinematic data to biomechanical signals such as those described in the system and method for characterizing biomechanical activity described in U.S. patent application Ser. No. 15/282,998, titled "SYSTEM AND METHOD FOR CHARACTERIZING BIOMECHANICAL ACTIVITY", filed 30 Sep. 2016, which is hereby incorporated in its entirety by this reference.

The kinematic measurements collected by the activity monitoring device are preferably along a set of orthonormal axes (e.g., an x, y, z coordinate system). The axis of measurements may not be aligned with a preferred or assumed coordinate system of the activity. Accordingly, the axis of measurement by one or more sensor(s) may be calibrated for analysis. One, two, or all three axes may share some or all features of the calibration, or be calibrated independently. The kinematic measurements can include acceleration, velocity, displacement, force, angular velocity, angular displacement, tilt/angle, and/or any suitable metric corresponding to a kinematic property or dynamic property of an activity. Preferably, a sensing device provides acceleration as detected by an accelerometer and angular velocity as detected by a gyroscope along three orthonormal axes. The set of kinematic data streams preferably includes acceleration in any orthonormal set of axes in three-dimensional space, herein denoted as x, y, z axes, and angular velocity about the x, y, and z axes. Additionally, the sensing device may detect a magnetic field through a three-axis magnetometer.

Generating a set of biomechanical signals based on the kinematic data functions to process and/or parameterize a set of characterizations of motion properties of an activity. The biomechanical signals for an activity are preferably a substantially real-time assessment of the biomechanical properties during the activity, and, as such, the biomechanical signal can be a time series data set (i.e., a temporal record). Biomechanical signals could alternatively be generated from pre-recorded kinematic data. Generating a set of biomechanical signals can include normalizing kinematic data or otherwise preparing the kinematic data for processing. Normalizing can involve standardizing the kinematic data and calibrating the kinematic data to a coordinate system of the participant or a piece of equipment. Preprocessing may additionally rectify relative orientations of multiple sensor devices mounted at different points. Single and double integration in combination with error correction can be used with the accelerometer data and gyroscope data along one or more axes. In some cases, right/left detection can be used to differentiate between biomechanics of different sides of the body. The biomechanical signals can reflect ranges in observed metrics and/or maximum, minimum, or average metric values. In some cases multidimensional motion paths can be generated to reflect the state of a kinematic property as a function of time during an action as shown in FIG. 3. For example, running path could show the motion path of a participant's hip when running or a golf swing path could show the three-dimensional path of an activity monitoring device during a golf shot.

Part of generating a biomechanical signals can include isolating kinematic data associated with an action of an activity, which may include segmenting the kinematic data and/or identifying and selecting a window of kinematic data associated with an action.

Figure 9:
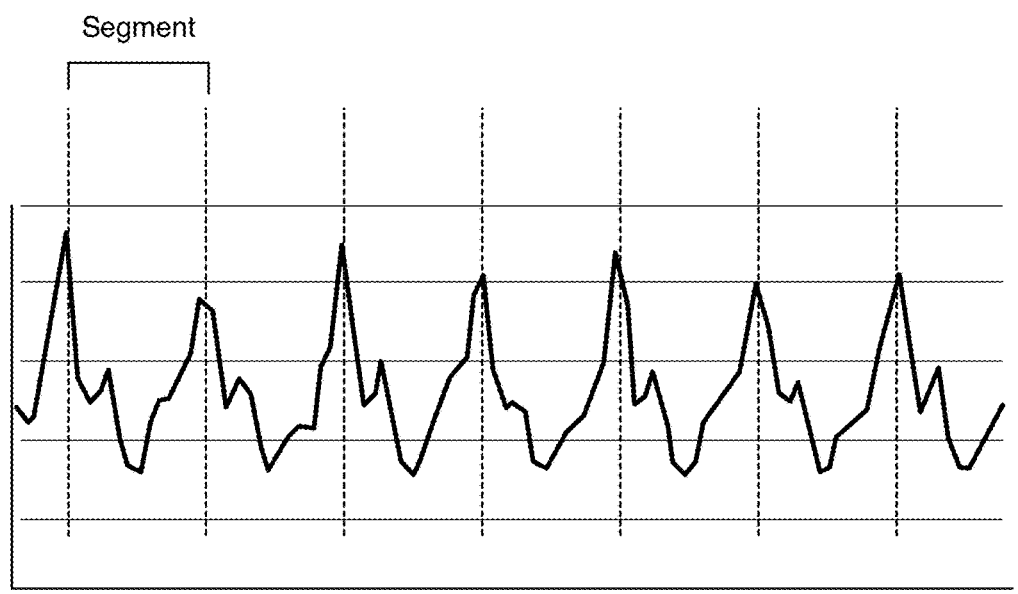
FIG. 9 is a schematic representation of segmenting kinematic data.

In the variations where the activity includes repetitive actions, generating a set of biomechanical signals can include segmenting the kinematic data as shown in FIG. 9. The kinematic data stream are preferably segmented into a consecutive sequence of actions. Biomechanical signals can be generated that reflect the biomechanical or motion properties observed within the action segments. In a running activity, segmenting can be executed for individual steps or for a stride (two consecutive steps). In a swimming activity, segmenting can be executed for individual arm strokes, individual leg kicks, or other appropriate action segments. In a biking activity, segmenting can be executed for individual pedal strokes.

Figure 10:
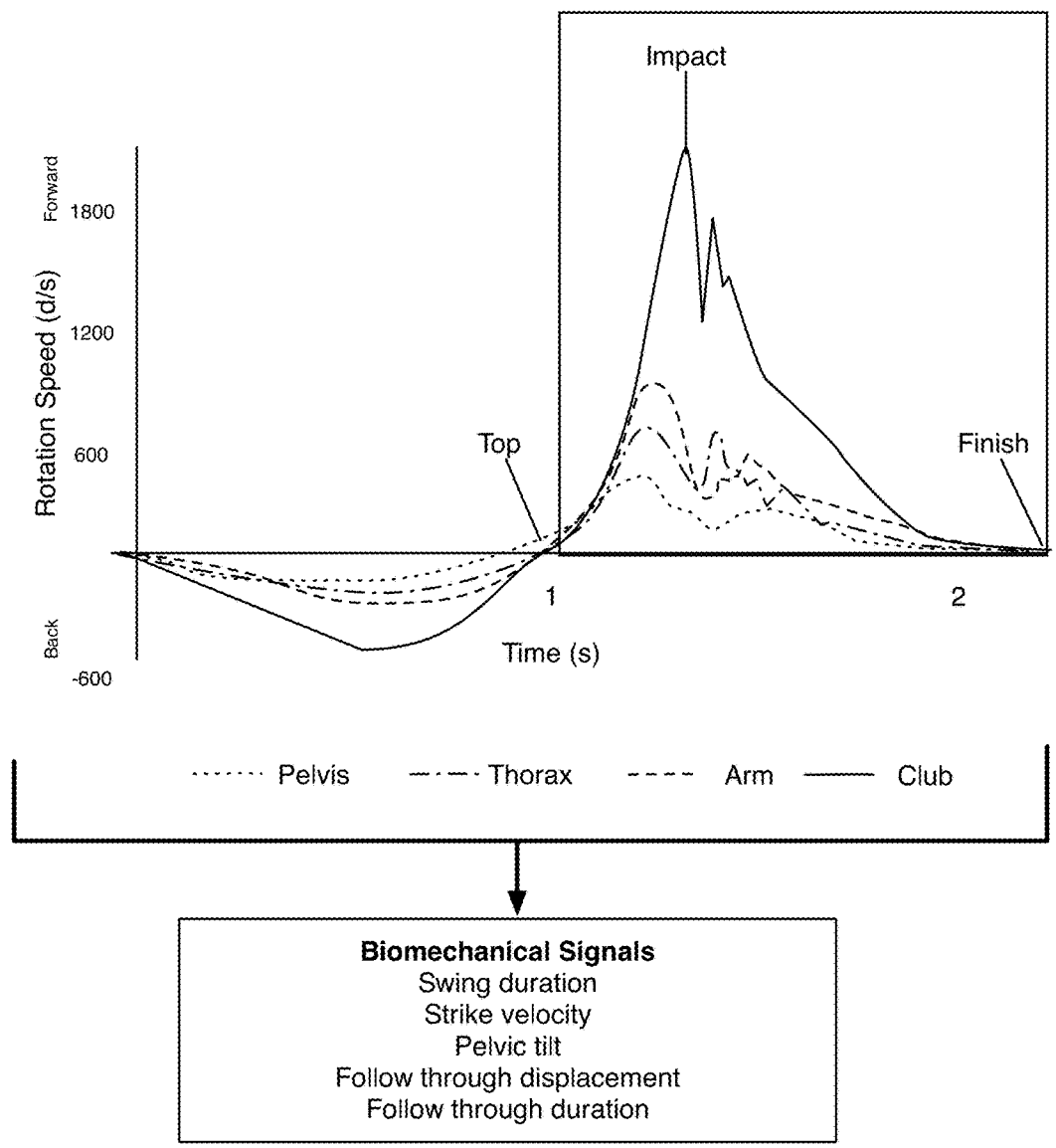
FIG. 10 is a chart representation of an exemplary golfing kinetic sequence and selecting a window of kinematic data.

In variations where the activity includes isolated actions, generating a set of biomechanical signals can include identifying the action. More specifically, identifying the action comprises identifying and selecting a window of kinematic data associated with an action and generating biomechanical signals from kinematic data within the window as shown in FIG. 10. In one variation, identifying the action can comprise monitoring the kinematic data, the biomechanical signals, and/or performance features as a function of time and detecting an action pattern. Detecting an action pattern can include the use of heuristic-based models such as monitoring value threshold conditions, event sequences, and/or other patterns. Detecting an action pattern can additionally or alternatively use machine intelligence such as deep learning, machine learning, statistical methods, and/or other suitable algorithmic approaches to detecting an action. Detection of an action may be made in real-time but may alternatively be retroactive where the action is detected and processed using data before, during, and after the action. For example, biomechanical signals may be actively collected as a participant is playing basketball. Most of the kinematic data may be ignored with regard to creating a jump shot biomechanical signals, but upon attempting a jump shot the patterns in the kinematic data are classified as a jump shot action, and the jump shot action can be used in generating biomechanical signals. In one variation, detecting an action pattern may include detecting an initial body position and the transition into an intermediary position of the action. In a golfing example, the ready stance of a golfer before swing could be detected based on the orientation of the activity monitoring device and then counting the action as the subsequent activity.

In golf, baseball, and other sports there may additionally be an impulse event that can be detected, wherein an impulse could correspond to hitting of a golf ball, hitting of a baseball with a bat, or some other event that causes a sudden change in load or forces. The impulse event could be detected through the kinematic data, but the impulse event could additionally or alternatively use audio data or other sensing capabilities of the system.

In another variation, identifying an action may be through receiving a user-initiated signal. For example, a participant may activate a swing recording mode within an application that is in communication with an activity monitoring device.

For a runner, a set of running biomechanical signals can include motion paths, ground contact time, cadence, braking, pelvic rotation, pelvic tilt, pelvic drop, vertical oscillation of the pelvis, forward oscillation, forward velocity properties of the pelvis, step duration, stride or step length, step impact or shock, foot pronation, body loading ratio, foot lift, and/or other signals.

Cadence can be characterized as the step rate of the participant.

Ground contact time is a measure of how long a foot is in contact with the ground during a step. The ground contact time can be a time duration, a percent or ratio of ground contact compared to the step duration, a comparison of right and left ground contact time or any suitable characterization.

Braking or the intra-step in forward velocity is the change is the deceleration in the direction of motion that occurs on ground contact. In one variation, Braking is characterized as the difference between the minimum velocity and maximum velocity within a step, or the difference between the minimum velocity and the average velocity within a step. Braking can alternatively be characterized as the difference between the minimal velocity point and the average difference between the maximum and minimum velocity. A step impact signal may be a characterization of the timing and/or properties relating to the dynamics of a foot contacting the ground.

Pelvic dynamics can be represented in several different biomechanical signals including pelvic rotation, pelvic tilt, and pelvic drop. Pelvic rotation (i.e., yaw) can characterize the rotation in the transverse plane (i.e., rotation about a vertical axis). Pelvic tilt (i.e., pitch) can be characterized as rotation in the sagittal plane (i.e., rotation about a lateral axis). Pelvic drop (i.e., roll) can be characterized as rotation in the coronal plane (i.e., rotation about the forward-backward axis).

Vertical oscillation of the pelvis is characterization of the up and down bounce during a step (e.g., the bounce of a step).

Forward velocity properties of the pelvis or the forward oscillation can be one or more signals characterizing the oscillation of distance over a step or stride, velocity, maximum velocity, minimum velocity, average velocity, or any suitable property of forward kinematic properties of the pelvis.

Step duration could be the amount of time to take one step. Stride duration could similarly be used, wherein a stride includes two consecutive steps.

Foot pronation could be a characterization of the position/angle of a foot during a stride or at some point of a stride. Similarly foot contact angle can be the amount of rotation in the foot on ground contact. Foot impact is the upward deceleration that is experienced occurring during ground contact. The body-loading ratio can be used in classifying heel strikers, midfoot, and forefoot strikers.

The foot lift can be the vertical displacement of each foot.

The motion path can be a position over time mapped for at least one point. The position is preferably measured relative to the athlete. The position can be measured in one, two, or three dimensions. As a feature, the motion path can be characterized by different parameters such as consistency, range of motion in various directions, and other suitable properties. In another variation, a motion path can be compared based on its shape.

Additionally, the biomechanical signals can include left/right detection, which may be applied for further categorizing or segmenting of biomechanical signals according to the current step.

Various approaches may be used in generating particular biomechanical signals as discussed in the incorporated U.S. patent application Ser. No. 15/282,998.

As one example, a process for determining ground contact time functions to characterize how long a foot is in contact with the ground when walking or running. The ground contact time preferably provides a time-based measurement of how long a foot is in contact with the ground during a step. In one variation, the ground contact time can be estimated as a running average for both feet. For example, the average time duration a foot is in contact with the ground can be reported as a running average of the amount of time a foot is in contact with the ground for each step or stride. In another variation, the ground contact time may be reported for a first and second foot. The method may additionally identify the first and second foot as a right and left foot. In one variation, right and left differentiation can be accomplished through single-point activity sensing. Multipoint sensing could additionally be used in differentiating right and left biomechanical signals. A ground contact time can be reported for the right foot, and a ground contact time can be reported for the left foot. Additionally, a ratio of foot contact can be generated based on the comparison of the right and left foot ground contact times, which may function to indicate any favoring of one leg over another. The ground contact time can be reported as a time, but may alternatively be reported as a percentage of step duration.

Determining ground contact time in a first variation includes segmenting the vertical velocity data by steps and taking the difference between the time of the maximum vertical velocity and the time of the minimum vertical velocity within each step cycle. In this variation, the maximum vertical velocity is selected as an event corresponding to the time of when the foot leaves the ground (i.e., "toe-off"), and the minimum vertical velocity is selected as an event corresponding to when the foot makes initial contact (e.g., heel strike or initial contact) with the ground.

Determining ground contact time in a second preferred variation can include measuring the time difference between the minimum vertical acceleration and the time of the minimum vertical velocity, adjusted by a linear transformation or other transformation. The minimum vertical velocity will correspond to when an increasing vertical acceleration crosses zero. At lower sampling rates, the time when vertical acceleration crosses zero can be in between sample points. A linear interpolation between negative and positive values of vertical acceleration and identification of a zero point can be used to refine the minimum vertical velocity time. Similar interpolation may be applied to identifying a minimum vertical acceleration. In one variation, a three-point interpolation for a parabola or other quadratic may be used. In another variation, determining ground contact time can include measuring the time difference between the time of the minimum forward velocity and the time of the maximum forward velocity and applying a linear transformation.

In another variation, an additional sensor or sensors may provide kinematic data sensed at or near the foot. For example, a sensor may be worn on each shoe. Foot sensor data can be used to provide higher resolution or refinements to the above methods or provide additional kinematic events acting to identify the beginning or end of foot contact. The ground contact time may be determined using other suitable techniques.

As one example, a process for generating a biomechanical signal can determine a left-right classification of a biomechanical signal functions to differentiate between actions alternating between right and left sides. More preferably, this includes classifying segments as left- or right-sided actions. Variations of an action such as stepping with different legs can be classified as distinct biomechanical signals (or a sub-category of biomechanical signals). Left-right signals preferably refers to actions that alternate between a participant's left side and right side, but can similarly apply to any multi-sided action. The left-right signals can be applied to distinguishing between a step with a right leg and a step with a left leg for a walking or running activity. Left-right leg signals could also be used to distinguish between left and right swim kicks, left and right bike pedal pumps, or other leg actions. The left-right signals may additionally or alternatively be applied to actions performed by the right arm or left arm such as a swim stroke, a rowing stroke, or any suitable action. Herein, the left-right signals are described primarily from the running use-case perspective, but can be similarly applied to other use cases.

Detecting a left-right biomechanical signal preferably includes identifying side bias in the kinematic data and/or other biomechanical signals.

In one variation, the normalized kinematic data streams determine a vertical axis and a forward-backward axis. A left-right axis can be determined from these two perpendicular axes. Left and right strides can be determined by monitoring the angular oscillation at a pelvic sensing device during a step segment. Gyroscopic data providing angular velocity around a vertical axis through the sensor towards earth can be used. In one variation, the left foot is determined if the angular velocity at the beginning of the step segment around the vertical direction measured by the gyroscope is less than zero, otherwise the right foot is determined. The angular velocity can be inspected at the beginning of a step segment. The sum of angular velocities over a whole step could alternatively be used for detecting a bias. Once left and right steps are identified the alternating pattern can be assumed to continue during subsequent step segments. However, continuous or periodic left-right detection can be performed to correct or verify accurate classification of steps. Additionally, anomalies in kinematic data or biomechanical signals can trigger an event to perform left-right detection. For example, after a participant stops or trips, the biomechanical signals may satisfy a condition that restarts the left-right detection.

In one variation, left-right classification can be determined through a sensor device positioned on one leg of a participant. The kinematic forces may be felt more strongly in a side-biased sensor device. Stronger forces evident in the kinematic data during a foot contact point of a step segment can indicate that the monitored side is currently making a step. Two side-biased sensor devices with one on each side can further address the challenge of detecting the current side.

A left-right detection in one variation may be used in a variety of ways. Preferably, the left-right detection is used to classify the biomechanical signals of the step segments such that at least a subset of biomechanical signals are classified into left and right biomechanical signals. For example, there could be a left and right braking biomechanical signal, a left and right ground contact time, a left and right vertical oscillation, and a left and right forward oscillation. Health issues, form issues, strength issues, and other insights may be acted upon in performing left-right detection. The left-right detection may additionally be used in calculating other biomechanical signals. For example, the left-right oscillations may be corrected when calculating particular biomechanical signals such as pelvic rotations.

As another example, a process for generating at least one set of motion paths functions to create a dimensional map of movement of at least one point of the body. The kinematic data can include multi-dimensional linear acceleration and angular velocity data, which can be converted to relative displacement or velocity for one to three dimensions as a function of time. The motion path in one implementation is generated for an activity monitoring device at the waist region. When using multiple activity monitoring devices, motion paths can be generated for multiple points such as the waist and the lower right and left leg. The displacements are preferably calculated relative to the participant with some central point of the participant being used as a point of origin, which functions to remove real world displacements caused by the activity (e.g., running forward). Preferably, displacements are tracked along a coronal, sagittal plane and transverse plane as shown in FIG. 4. The displacement may alternatively be mapped to any suitable dimensional view. In one view, the instantaneous velocity at each point in the motion path can additionally be used to provide an extra dimension to the motion path. Pattern recognition algorithms, computer vision, image recognition, neural networks, and/or other suitable machine intelligence techniques can be used to analyze and characterize the shapes and variability of the motion paths created by the runner.

In addition to biomechanical signals, blocks S110 and S210 can include collecting activity contextual data S112/S212, which functions to collect other information related to the conditions in which the motion data is collected. Contextual data can include speed, location, altitude, temperature, degree of incline, surface conditions (e.g., road vs. dirt path), activity timestamp, heart rate, and/or any suitable information. In one variation, collecting activity contextual data can include collecting biological data. Heart rate, blood lactate levels, respiration levels, perspiration levels, and/or any suitable biological data can be collected. In some variations, contextual data may be collected only in block S110 to establish relationships between biomechanical signals and the contextual data. This can be used to build richer training data used in detecting fatigue. In one exemplary machine intelligence implementation, data is collected from runners' in a controlled environment and the runners' blood lactate data can be collected along with the biomechanical signal data. Machine intelligence can train on how to detect blood lactate from the biomechanical signals.

Figure 11:
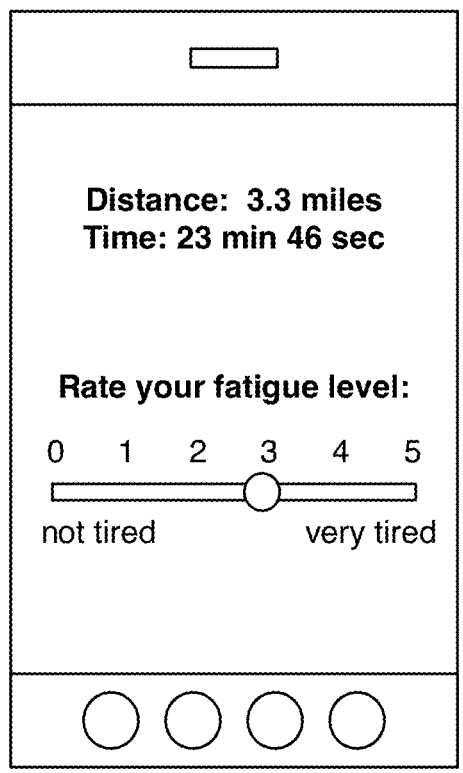
FIG. 11 is a schematic representation of an exemplary user application collecting a qualitative assessment of fatigue.

In another variation, the method may additionally include collecting a qualitative assessment from a participant S114, which functions to survey the participant on how they judge their fatigue level as shown in FIG. 11. The qualitative assessment is preferably a survey after completing an activity session. For example, a participant may be able to review their performance in a user application, make notes, and rate their tiredness level from zero to five. Characterizing the fatigue model can utilize the qualitative assessments.

Block S120, which includes analyzing temporal changes in the set of biomechanical signals and characterizing a fatigue model, functions to determine patterns and conditions for detecting fatigue. Fatigue can generally be detected by building a fatigue profile that models expected performance levels and patterns as exhibited by biomechanical signals.

Fatigue may be parameterized in a variety of manners. Preferably, at least one fatigue model is established that can detect when a participant is in a fatigued stated state. In one variation, fatigue state can be a binary state of not fatigued and fatigued. In another variation, fatigue state can be a continuous value. For example, a fatigue rating can use zero as a baseline where the participant is not observed as being fatigued, one when the participant is at the threshold of being classified as fatigued, and greater than one to indicate the magnitude of fatigue. In yet another variation, a set of different fatigue state classifications can be identified for some activity intensity level. There could be a non-fatigued state, which may characterize normal performance patterns. Another exemplary fatigue state could include discomfort state, which is a state in between comfortable normal non-fatigue state and a fatigue state, and another exemplary condition could include an injury risk state that includes a pre-injury state and/or other suitable type of injury state. An injury risk state can be a state where a high risk to injury is predicted, the onset of an injury is occurring, or an injury has been detected.

In a first variation, characterizing the pattern for fatigue includes collecting kinematic data and generating biomechanical signals across a range of conditions. Fatigue can be a function of current intensity and recent activity and so the pattern for fatigue may depend on several factors. Biomechanical signals and other activity related data could be collected to form a matrix of different conditions.

In characterizing the pattern for fatigue, machine intelligence can build up data used in classifying particular biomechanical signals as different fatigue states. Then, when a participant is performing an activity, the detected biomechanical signals, such as motion paths and associated data, can be used in determining the fatigue state. Additionally, machine intelligence can be developed to detect the transition from a comfortable state through increasing levels of intensity up to some degree of fatigue. In a motion path variation, a spectrum of motion paths associated with different intensity levels can be used in generating a measure of fatigue or conversely comfort level. In another variation a machine intelligence model can be developed to identify fatigue through the detection of degrading biomechanical signals.

A wide variety of machine intelligence approaches can be used in characterizing and detecting fatigue state.

A first potential approach can use a population classification model based on labeled data of fatigued and non-fatigued states. Such population classification models can include multi-layer neural networks, support vector machines, Bayes Nets, and deep learning networks to identify common characteristics of fatigue based on the population. By using a supervised machine learning algorithm on the population, the algorithm can generalize to new individuals and new behaviors.

A second potential approach can use a time-series classification model based on labeled data of fatigued and non-fatigued states. Time-series classification models can include recurrent neural networks, hidden Markov Models, dynamic Bayes Nets, and temporal deep learning networks to identify the fatigued states of an individual as one progresses through their run. By using a supervised machine learning algorithm on each individual, a tailored model can be used to detect the intricacies of each individual.

A third approach can use an unsupervised clustering algorithm to find groups of data that are most dissimilar. An unsupervised clustering model approach can include k-means, expectation-maximization algorithms, density-based clustering, principal component analysis, and auto-encoding deep learning networks to identify different states, which would correspond to fatigued and non-fatigued performance. By using an unsupervised learning algorithm, the model can find natural boundaries between the types of fatigued states.

These algorithms use all the data discussed previously, including biomechanical signals, motion paths, contextual data, and/or any suitable metrics. The various metrics can be used as features used in training and then in detecting fatigue. Various heuristics may additionally be used in combination with a machine intelligence approach. For example, a subset of features may depend on heuristic analysis of various aspects such as comparison of a biomechanical signal to a threshold (e.g., a binary feature of the biomechanical signal is greater than or less than a value), an analysis of a motion path, and/or any suitable heuristic-based analysis. The used heuristics are preferably selected because of a correlation to fatigue, but the machine intelligence approach may be used to determine when and how to use them when detecting fatigue state.

Alternatively or additionally, a heuristic-based approach can set various thresholds used in detecting fatigue through rule based patterns.

Figure 18A:
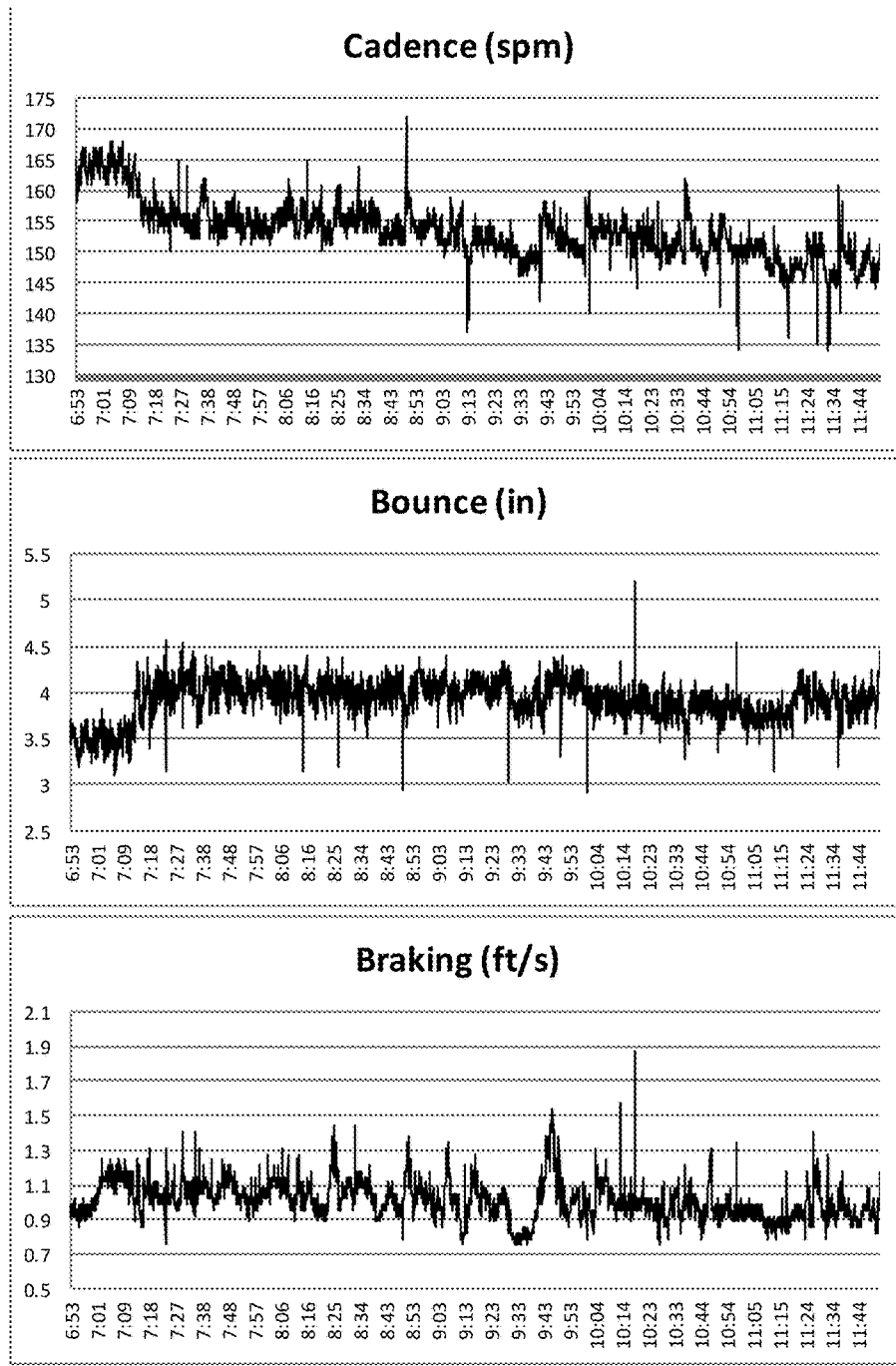
FIGS. 18A-18C are charts of exemplary biomechanical signal data charted over the course of a run.
Figure 18B:
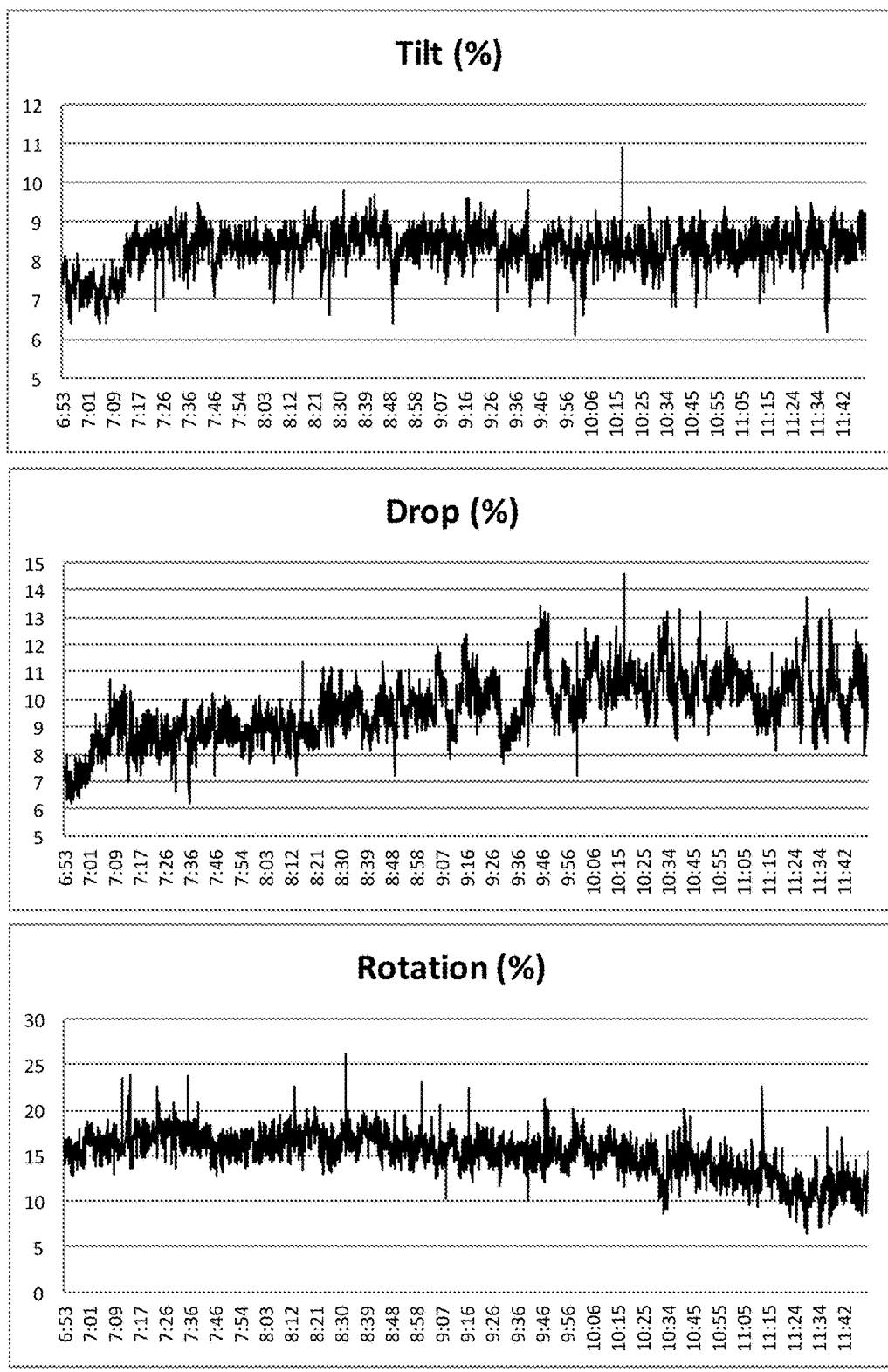
Figure 18C:
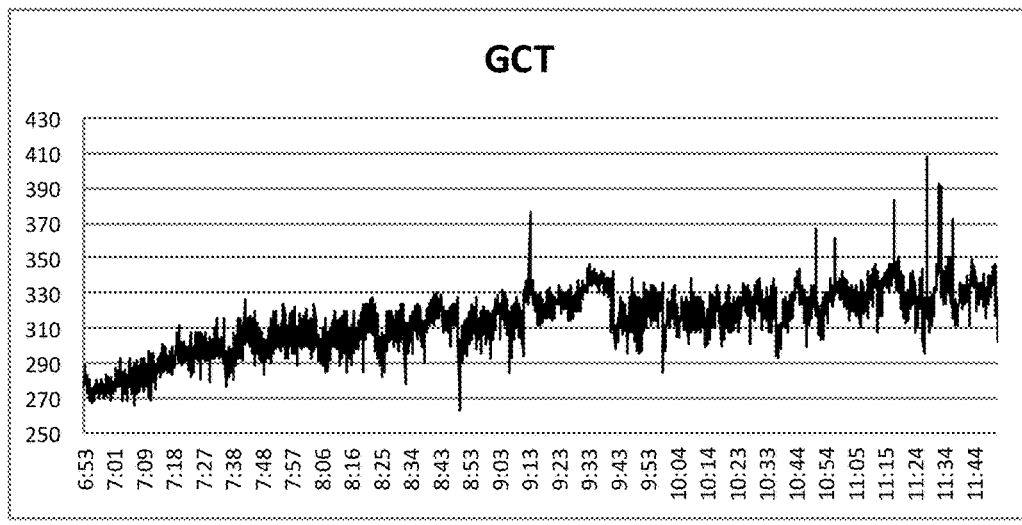

A heuristic-based approach preferably includes the analysis of one or multiple biomechanical signals. Biomechanical signals change over the course of an activity. Biomechanical signals such as cadence, vertical oscillation (i.e., "bounce"), braking, pelvic/sagittal tilt, pelvic/frontal drop, pelvic/transverse rotation, and ground contact time experience different transformations over the course of a run as shown in the exemplary biomechanical signal run data in FIGS. 18A, 18B, and 18C. In a running use case, an exemplary set of heuristic-based analyses can include monitoring changes in ground contact time, monitoring changes in sagittal tilt range of motion, consistency of biomechanical signals, changes in cadence and/or various motion path heuristics. Other suitable heuristic-based analyses may additionally or alternatively be used.

For example, the median value and value distribution of a biomechanical signal as a function of distance could be stored so that fatigue can be calculated when the user significantly deviates beyond these expectations (e.g., greater than two standard deviations).

In one implementation, a heuristic-based fatigue model is based on the ground contact time as a function of running activity. Running activity may be a metric based on running time, distance, steps, or other suitable measures of the activity session. The fatigue model is preferably configured to verify that the current ground contact time of a participant during an activity session is above a threshold value and/or that the variance of the current ground contact time is above a variance threshold. The value threshold and the variance threshold can be set based on standard defaults but is preferably set based on the history of the participant. Ground contact time will generally be seen to increase as a function of fatigue or tiredness. A threshold value may be determined or identified that can be used as a ground contact time value condition. The threshold value can be globally set by default, may be set for a particular class of people, but may additionally be determined for a particular participant. Similarly, variance of ground contact time may increase as a function of fatigue. A variance threshold may be determined or identified that can be used in a ground contact time variance condition. Preferably, when the variance of ground contact time exceeds the variance threshold, then that may signal potential fatigue. Alternatively, a ground contact time value and variance may be inputs into an alternative function.

Similarly, a heuristic-based fatigue model may be based on sagittal tilt and/or range of motion. Sagittal tilt will preferably increase with fatigue similar to ground contact time. A heuristic approach may use a sagittal tilt value condition and/or sagittal tilt variance condition, which depend on a sagittal tilt threshold value and a sagittal tilt variance threshold.

In another variation, a heuristic-based fatigue model may be based on cadence. Cadence may decrease with fatigue. A heuristic approach may use a cadence value condition and/or cadence variance condition, which depend on a cadence threshold value and a cadence tilt variance threshold. In these conditions, fatigue may be indicated by cadence dropping below the cadence threshold and cadence variance going above a cadence variance threshold.

Other biomechanical signals could similarly be used in a heuristic-based analysis such as value conditions, threshold conditions, and/or other suitable condition functions. Signal increases, decreases, and/or other signal patterns may be detected as signs of fatigue in various biomechanical signals.

Users could be given initially calibrated thresholds based on demographic information. Biomechanical signal value thresholds and variance thresholds can be set. Another threshold could be time window threshold that is used to measure the amount of time a user is surpassing the specific threshold before it indicates fatigue. The thresholds can change overtime based on machine learning techniques that get better as each individual runs or as more information is collected from different populations of users with the device. For example, during a run baseline biomechanical signals and motion path signals are collected. The baseline can be compared to the instantaneous biomechanical signals and motion paths. The instantaneous signals will degenerate as the user fatigues. A fatigue state or level can be dynamically detected from this comparison.

In another implementation, a fatigue model can be configured based on patterns in one or more motion paths. Participants will generally have moving patterns that are unique but generally consistent between activity sessions. A fatigue model may correlate the shape of a motion path with different fatigue states under various conditions. Preferably, motion paths are analyzed with motion paths under similar conditions. For example, a motion path of a participant may be compared against a motion path associated with a similar running speed. Other activity conditions that may be used may include incline, terrain type, or other suitable conditions. For example, there may be different motion paths for different inclines.

In one implementation, motion paths are analyzed based on a set of motion path heuristics. In one approach, motion paths can be compared against an elliptical model (i.e., a set of motion path or "loopiness" heuristics). An ellipse is preferably used as the base shape for the sagittal plane. Alternative shapes or paths could similarly be used. When running, an activity monitoring device attached to the user in the pelvic region will experience generally elliptical motion. The observed motion path can deviate from this with variations in form and fatigue level.

Figure 19:
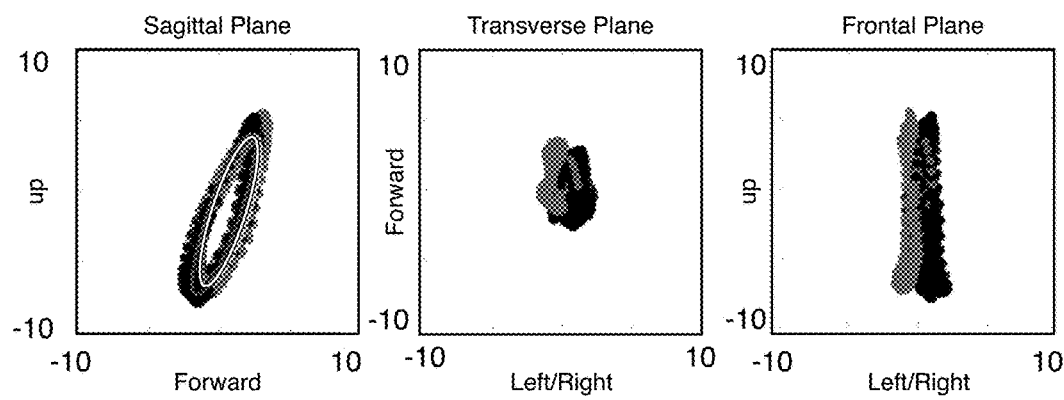
FIG. 19 is a schematic representation of analyzing motion path properties.

As shown in FIG. 19, using a set of motion path heuristics include fitting an ellipse to a motion path and analyzing the ellipse to the motion path. Analyzing the ellipse can include measuring a major axis, measuring the minor axis, measuring the angle, measuring the root mean squared error, measuring the x-offset, and the y-offset. The root mean squared error can be an indicator of the consistency or "fuzziness" of a motion path. A more consistent motion path will generally have a lower root mean squared error value. The x-offset and y-offset can relate to the amount of variation (i.e., wiggle) in the motion path. The set of motion path heuristics may be used on a motion path data that is a combination of right and left data. Alternatively motion path heuristics can be used for the right side and left side independently.

As mentioned above heuristic approaches may be used in combination with machine intelligence. For example, one or more heuristic-based signals may be a feature input into a machine learning algorithm in combination with biomechanical signals or other feature inputs. Accordingly heuristic-based signals use as feature inputs can include monitored changes in ground contact time, monitored changes in sagittal tilt range of motion, consistency state of biomechanical signals, changes in cadence and/or various motion path heuristics.

In one variation, characterizing a fatigue pattern can include identifying biomechanical challenges of a participant, wherein a biomechanical challenge is characterized with a biomechanical property that a participant struggles with during the activity. A biomechanical challenge may be identified as one that is significantly below or above an expected or target performance metric. For example, a participant may run with a cadence that is below a target range. A biomechanical challenge may also be a biomechanical signal that degrades before other biomechanical signals. After observing a participant on multiple activity sessions, the method could characterize which one or more biomechanical signal changes first and most significantly. By identifying a biomechanical challenge, monitoring of those particular biomechanical signals can be given more weight in detecting fatigue state.

In other implementations, a fatigue model can be based on multiple biomechanical signals. In one example, a fatigue model for running can utilize the biomechanical signals ground contact time, braking, pelvic rotation, pelvic tilt, pelvic drop, vertical oscillation of the pelvis, forward velocity properties of the pelvis, and left-right detection. Other combinations of biomechanical signals may alternatively be used. In one variation, multiple biomechanical signals in addition to activity contextual data can form a set of features that can be processed by a neural net or other suitable machine intelligence process.

When a fatigue model is established, the method can be applied to actively detecting and responding to fatigue during an activity session which includes collecting kinematic data and generating at least one biomechanical signal S210, monitoring the fatigue state through processing the at least one biomechanical signal according to the fatigue model S220, and triggering feedback to a user interface in response to a fatigue model S230. As noted, fatigue detection can be performed while also updating the characterization of a fatigue model, wherein a fatigue model can be continuously or periodically updated as more data is collected.

Block S210, which includes collecting kinematic data and generating at least one biomechanical signal, functions to obtain motion data of a participant used to analyze fatigue. As discussed above, Block S210 is substantially similar to block S110.

Block S220, which includes monitoring the fatigue state through processing the at least one current biomechanical signal according to the fatigue model, functions to detect the state of fatigue based on the movements of a participant. The fatigue model may depend on a particular set of inputs, and the inputs include at least a subset of biomechanical signals. The inputs may additionally include activity contextual data (e.g., terrain conditions). Monitoring of biomechanical signals preferably analyzes the current state of biomechanical signals for changes or patterns indicative of a fatigue state. Machine intelligence and/or heuristic-based approaches may be used and preferably corresponds to the approaches applied in Block S120 above. Additionally, the monitoring of a fatigue model may depend at least partially on previously collected data but could alternatively dynamically detect fatigue without direct reliance on previously collected data.

Figure 12:
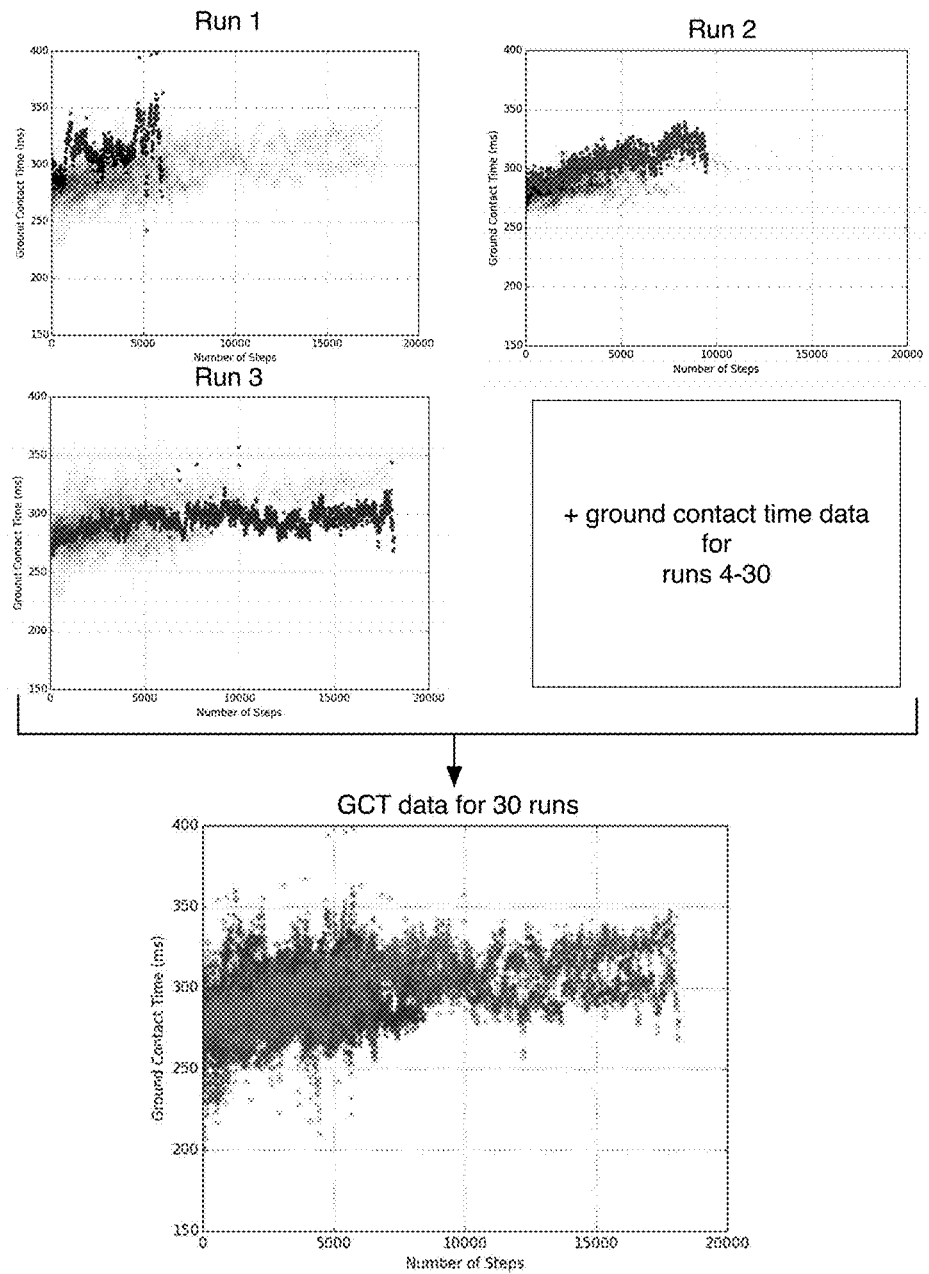
FIG. 12 is a schematic representation of combining ground contact time data when characterizing a fatigue model.
Figure 13:
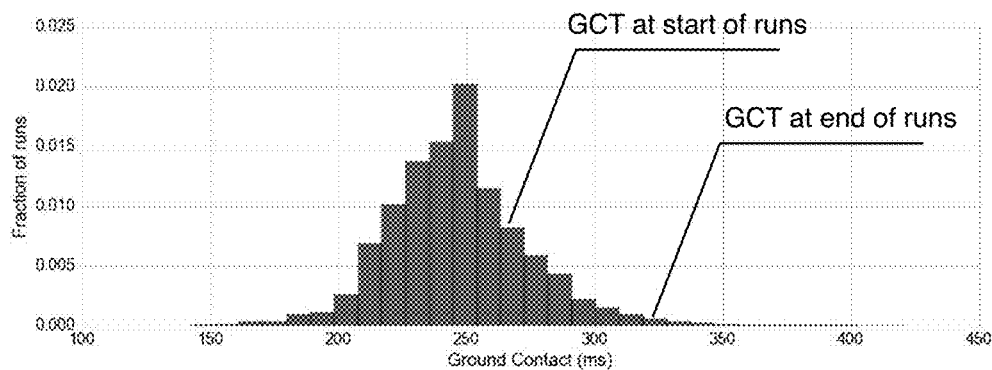
FIGS. 13 and 14 are graphical representations of base value and variance values changing with fatigue.
Figure 14:
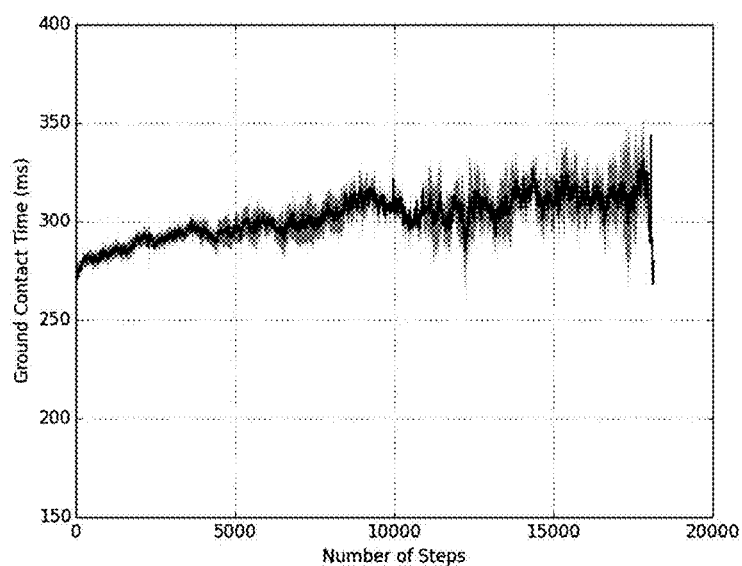

In one heuristic-based fatigue model established in block S100, monitoring the fatigue state can include processing a value threshold and a variability threshold on the biomechanical signals such as ground contact time, sagittal tilt, cadence or motion paths. In particular, monitoring a biomechanical signal can include detecting a value change and/or a variance change in one or more biomechanical signals over the duration of an activity session (e.g., a run). As an example we will use ground contact time as an exemplary biomechanical signal, but such approaches can be applied to any suitable biomechanical signal. As shown in FIG. 2, a participant will have general patterns in ground contact time. Ground contact time will generally increase during a run as the runner begins to fatigue. The rate of change, the amount of change, and/or the values encountered during a run may be used in detecting a fatigue condition of a fatigue model. When the ground contact time is within a normal range then it may be detected that the participant is in a non-fatigued state. A state of fatigue is preferably identified by identifying the base value of ground contact time and/or the variance in ground contact time to surpass a value threshold and variance threshold respectively. The threshold values may be set and/or updated for each participant. As shown in FIG. 12, the ground contact time data of multiple runs can be analyzed as a whole to determine a fatigue model. As shown in FIG. 13, the ground contact time at the start and end of a run will generally differ if the participant exerted himself or herself. Similarly, as shown in FIG. 14, the variance in ground contact time increases with the duration of a run and the level of fatigue. A potential injury state may be identified by sudden changes in the ground contact time, imbalances of ground contact time between the right and left sides, surpassing an injury threshold, or when the cumulative activity within a fatigue state surpasses a total threshold. Additional or alternative biomechanical signals can similarly be monitored.

In a variability threshold heuristic a baseline variability threshold established as part of the fatigue model in Block S100 can be compared to a current variability score. A current variance score is preferably a running average of recent biomechanical signals over a small time window or number strides. Recent activity may be defined in a variety of ways depending on implementation. It may, for example, include activity in the last minute, last fifty steps, or other suitable windows. The difference of the baseline and current variance values is calculated. The variability threshold heuristic can indicate a fatigue state if the difference is greater than a particular threshold. Additionally, a heuristic-based fatigue model may additionally include a time threshold heuristic. The time threshold heuristic looks at how long a runner appears to be fatigued based on the variance values. If the runner is running with fatigue-level variance greater than a time threshold then the runner can be determined to be in a fatigued state. The time threshold functions to accommodate for normal variance in running motion during terrain changes and other temporary changes.

In one example, a variability score can be the variance of recent ground contact time (or any suitable biomechanical signal). In another example, a variability score may be a computer vision or other data analysis process that characterizes how much variation occurs in a motion path biomechanical signal. For example, a runner who consistently strides with the same exact motion will have a small variance score. A runner who swings his legs in a different motion every stride will have a large variance score.

In another exemplary implementation, monitoring a biomechanical signal can include detecting a change in motion path patterns. Motion paths may provide a more readily characterized biomechanical pattern for non-fatigued state regardless of personal tendencies. The basic motion pattern of an individual will generally be consistent at the beginning of an activity session. Changes in patterns of a motion path may be associated with fatigue. A motion path from an earlier part of an activity session may be used during the current activity session as a reference for dynamically determining fatigue state. A fatigue state may be detected by detecting pattern changes by performing pattern classification processes to compare a current motion path to a reference motion path. In one preferred implementation a motion path may be analyzed through fitting an ellipse and generating the motion path properties of: major axis length, minor axis length, angle of ellipse, root mean squared error, x-offset, and/or the y-offset. The motion path properties can be used as alternative motion path biomechanical signals for which value/variance threshold heuristics can be used and/or machine intelligence analysis. Motion paths may alternatively be used in other suitable manner in a two dimensional or three dimensional form.

Detection of a change in biomechanical signals, such as ground contact time, sagittal tilt, cadence or motion paths, can additionally or alternatively use various machine learning techniques. In one variation, a comfort level of a biomechanical signal can be determined in some manner. For example, the biomechanical signals of a participant during the initial stages of an activity session can be set as a comfort motion path. Using comfort level of the biomechanical signals as a reference, changes in the biomechanical signals can be monitored for particular traits such as a shift in the base value, recent value variance, shape changes in a motion path signal, rate of changes, and/or other suitable metrics. When operating within a comfort level there may be a gradual divergence in the motion paths.

As described above, a hybrid implementation can use machine intelligence in combination with a heuristic approach. In one hybrid implementation, various heuristic-based analyses of biomechanical signals can be used as feature inputs into a machine learning algorithm as described above. In another hybrid implementation, the heuristic approach can be used, and then the heuristic model can be improved as more data is collected about a particular runner or runners in general. For example, the signal value thresholds and/or variance thresholds may be refined to better correspond with the normal performance of the user.

Block S230, which includes triggering feedback in a user interface in response to a fatigue model, functions to apply a transformative change to the activity. Block S210 and S220 can enable fatigue level of a participant to be determined efficiently and, in some implementations, in real-time. A variety of unique applications can be built on top of fatigue detection and/or measurement including providing analysis of fatigue in relationship to the activity, notifying the participant, enhancing exercises by hitting targeted fatigue levels, providing guidance on participant actions, warning of potential injury, and/or other applications.

Providing analysis of fatigue in relationship to the activity functions to extract insights and information relating the kinematic data and awareness of fatigue associated with the kinematic data. Providing analysis can include itemizing changes that occur when a participant is fatigued. A user application can present changes in the biomechanical signals, changes in the motion paths, the type of changes that happen in different environmental conditions, performance changes (e.g., running speed) and other suitable information. Analysis can be provided by displaying information, generating a graphical representation (e.g., a chart, a graphical indicator, etc.), playing audio feedback (e.g., making an speech audio announcement concerning the changes), activating a haptic feedback device, or using any suitable mechanism to provide feedback.

In some variation, analysis and triggering feedback in a user interface can include generating activity route options based on the fatigue state of a participant. This variation preferably includes predicting fatigue state based on current biomechanical signals. The predicted fatigue state may be used in providing pacing and distance targets before or during an activity session. For example, before starting a run, the method may recommend a distance and a target mile split time so as to hit an acceptable (non-injury) fatigue state. The predicted fatigue state can alternatively be used in generating a map of running route options using a prediction of the current biomechanical signals satisfying a fatigue condition in a fatigue model and/or selecting a recommended route for the participant. The prediction can use previous activity history and current status to determine when a participant would experience fatigue. The prediction may additionally account for a planned running route and terrain on that route.

Figure 15:
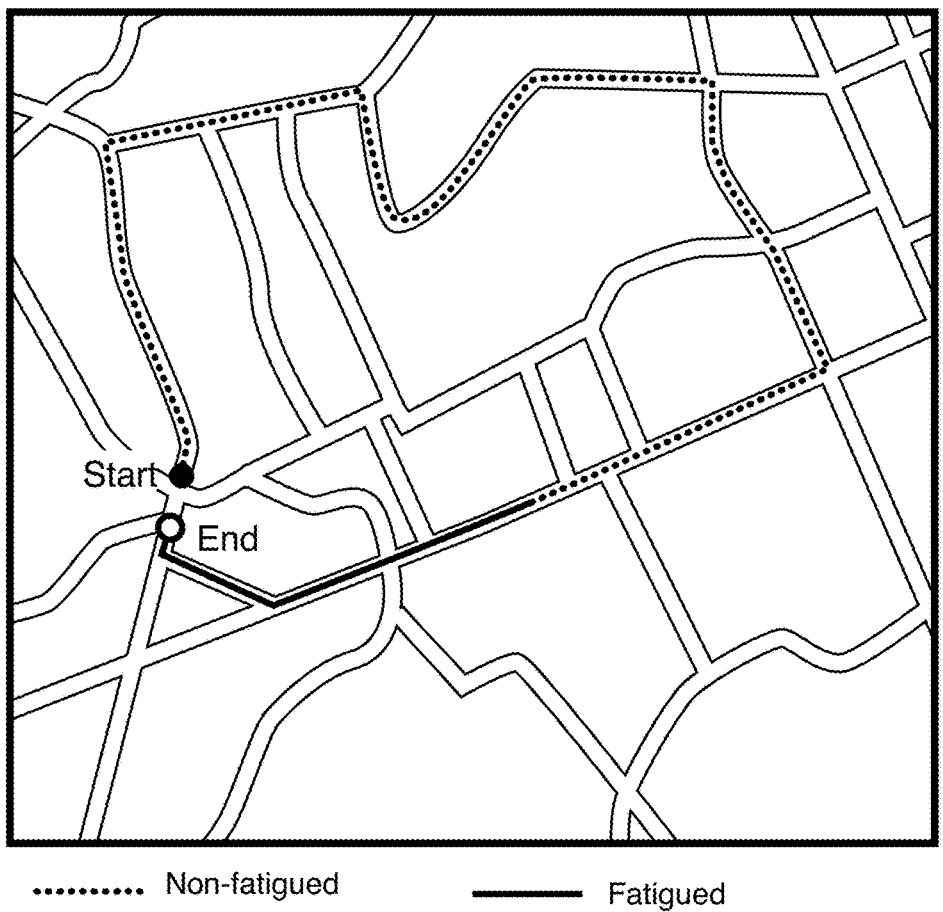
FIG. 15 is a schematic representation of an exemplary routing option representing predicted fatigue on a map.

In one implementation, a participant could access a map before or during an activity session and see a map with an indication of where they can run (or walk, bike otherwise go) before fatigue may set in as shown in FIG. 15. In this way, a participant could plan their route accordingly. In another implementation, triggering user feedback can include directing a participant on a route selected based on the predicted fatigue state. For example, a user application could tell a participant where to run based on expectations on fatigue. This route planning could be combined with training objectives such as pace and distance to target different fatigue states at different times.

Providing analysis can additionally include determining a top comfort-speed. The top comfort-speed is a rate at which a participant can operate at without expressing kinematic traits of fatigue. The top-comfort speed may additionally be a speed at which injury is less likely compared to higher speeds and endurance is higher. Performing an activity at the top comfort-speed can provide a useful performance goal for a participant. Similarly, increasing the top comfort-speed can be useful performance goal.

Figure 16:
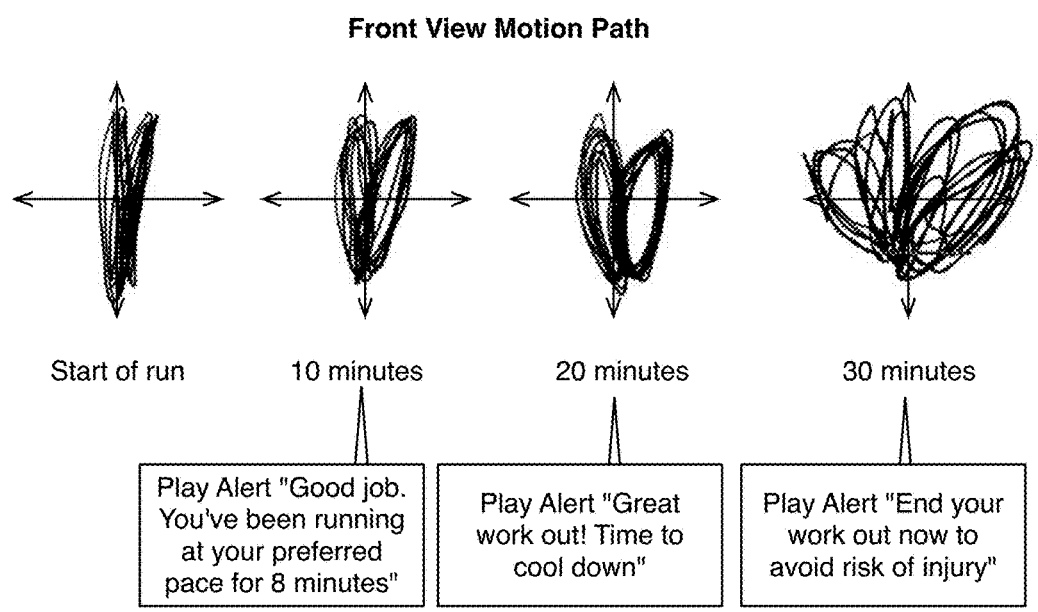
FIG. 16 is a schematic representation of an exemplary motion path biomechanical signal being used in displaying real-time feedback based on different fatigue states.

Notifying the participant preferably provides some real-time information as shown in FIG. 16. Real-time information is preferably provided through audio coaching using text-to-speech processing and/or pre-recorded messaging. Real-time information can be provided through graphical or textual information displayed on a computing device. The form and objective of the notification can vary. In one variation, notifying the participant can include signaling when a participant is in the "zone" or operating at or substantially near a peak performance state (e.g., running in a top comfort-speed range). Similarly, notifying the participant can include signaling a warning when the participant is nearing or at a fatigued state. In some cases, the fatigue model can detect a fatigue state that relates to the lactate turn point associated with when fatigue sets in for a participant. An audio cue could be played telling the participant to reduce the intensity to avoid injury. In another variation, notifying a participant can include presenting a graphical representation of performance during different levels of fatigue. Motion path graphics can be generated and provided which provide a graphical visualization of the biomechanical changes when a user is fatigued. In other implementations, the notification may simply indicate imbalances. For example, an audio cue can indicate that a participant should lift their right foot more during each stride to balance out their running stride.

The method may additionally provide injury warning in addition to or as an alternative to fatigue detection. Injury warning can include detecting a biomechanical shift satisfying an injury indicator condition as shown in FIG. 16. Injury warning may be detected in a substantially similar manner to detecting a transition to fatigue except the conditions of an injury risk state would differ from a fatigue state. Generally, fatigue model will be based on detecting performance outside of the normal performance range of a participant but within expectations of that participant. A participant will typically gradually transition into a fatigue state after some period of activity. An injury condition, however, may be detected through unexpected deviations in performance. One pattern of injury may be detected based on a change in biomechanical signals beyond an expected range. For example, the cadence of a participant may suddenly drop dramatically beyond a threshold. Another pattern of injury could be an introduction of asymmetry between left and right biomechanical signals. For example, the ground contact time for the right foot may gradually grow more than the ground contact time of the left foot indicating limping. In some cases, fatigue may be quantified over a time duration and used as an injury indicator condition. In one example, if an individual continues to run after the onset of fatigue and runs for more than a particular time threshold, an injury warning could be triggered. Similarly, the level of fatigue can be quantified for a participant over multiple activity sessions. In this variation, an injury prevention warning could be triggered if the participant has been overexerting himself or herself recently.

Providing guidance on participant actions functions to coach a participant or elite runner. Providing guidance can include setting performance targets and specific training plans based on previous historical training runs or race competitions. In the case of running, the performance targets and training plans can be running speed, duration, cadence and other biomechanical signals and/or conditions that can help the runner from fatiguing prematurely during a long race event. The performance targets could be distinct goals that can be tracked. The performance targets can alternatively be activity session plans. A running session plan can be a sequence of different stages, which a participant can follow. For example, various fartlek or interval training sessions may be generated that determine for the duration and intensity of the activity at different times during the session. The guidance can additionally be supplied in realtime during an activity. For example audio instructions could be delivered telling a participant to run faster or slower based on the participant's fatigue state. Similarly, providing guidance can include suggesting a route change based on fatigue level. For example, a participant could be automatically directed to run up a hill or along a flatter path depending on the level of fatigue.

As one particular application, the method may be used in providing strengthening exercises to strengthen muscles that experience an earlier onset of fatigue. As discussed above, the method and application of the fatigue model can include detecting biomechanical challenges. These are preferably biomechanical signals that degrade and/or move out of a target range before other biomechanical signals. Biomechanical properties that are identified as a challenge may be prioritized for training recommendations. Coaching can be delivered during an activity to encourage a participant to focus on getting a particular biomechanical signal to a target range. Additionally post-activity exercises can be provided that target particular muscles.

Figure 17:
FIG. 17 is a schematic representation of an interval training plan based on fatigue levels translated into participant activity.
Figure 17:
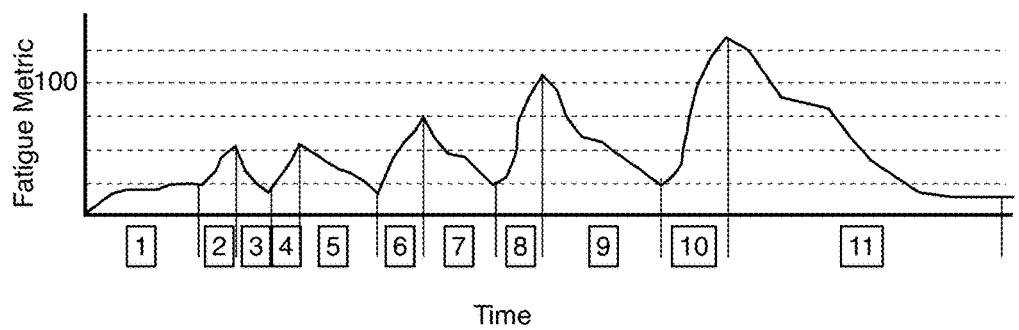

In one implementation, triggering feedback in the user interface comprises setting a training recommendation within a user interface to target a particular fatigue state within the activity session. As discussed above, different fatigue states can be detected. In one variation, temporal changes in the biomechanical signals can be analyzed to characterize a non-fatigued condition. Training recommendations can target non-fatigued conditions and fatigued conditions. In interval training sessions, the training recommendations can transition between satisfying a fatigue state and a non-fatigue state multiple times as shown in FIG. 17. The duration in a non-fatigue state or a fatigue state can be modified to produce different training results. In one variation, the rate to go from a non-fatigue state to a fatigue state could be a metric targeted or used in setting training recommendations during training or used The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for utilizing an activity monitoring device comprising:
   setting a fatigue model based on kinematic data collected from an activity monitoring device and generating a temporal record of at least one past biomechanical signal that is calculated from the kinematic data, wherein the temporal record includes a plurality of ground contact times; and
   during an activity session:
      collecting current kinematic data of a participant and generating at least one current biomechanical signal from the current kinematic data, wherein the at least one current biomechanical signal includes ground contact time,
      monitoring a fatigue state through processing the at least one current biomechanical signal according to the fatigue model, wherein processing the at least one current biomechanical signal according to the fatigue model comprises verifying that the current ground contact time is above a base threshold derived from the temporal record including the plurality of ground contact times to confirm that the participant is experiencing a fatigue event and verifying that variance of the current ground contact time is above a variance threshold derived from the temporal record including the plurality of ground contact times to confirm that the participant is experiencing a fatigue event, and
      triggering feedback in a user interface based on the fatigue state, wherein the fatigue state is represented by one of a plurality of fatigue levels, including a non-fatigue level, a discomfort fatigue level, and an injury risk fatigue level, and wherein the feedback comprises a suggestion of how the participant should alter his or her activity to manage the fatigue state being endured by the participant, wherein the suggestion is specific to each one of the plurality of fatigue levels.

2. The method of claim 1, wherein the at least one current biomechanical signal includes ground contact time of a running activity.

3. The method of claim 1, wherein setting the fatigue model comprises:
   during a set of initial activity sessions, collecting the kinematic data from an activity monitoring device and generating a temporal record of at least one biomechanical signal that is calculated from the kinematic data; and
   analyzing temporal changes in the biomechanical signals during the initial activity sessions and characterizing the fatigue model.

4. The method of claim 3, further comprising, for at least a subset of the initial activity sessions, collecting qualitative assessments of fatigue from a participant after completion of an activity session; and wherein characterizing a fatigue model accounts for qualitative assessments.

5. The method of claim 1, wherein the at least one current biomechanical signal includes a kinematic motion path.

6. The method of claim 5, wherein monitoring the at least one current biomechanical signal comprises detecting a fatigue state through pattern changes in a kinematic motion path.

7. The method of claim 1, wherein the at least one biomechanical signal and the at least one current biomechanical signal includes at least one of cadence, braking, pelvic rotation, pelvic tilt, and pelvic drop.

8. The method of claim 1, wherein said triggering feedback in the user interface comprises setting a training recommendation within the user interface to target one of the plurality of fatigue levels within the activity session.

9. The method of claim 8, further comprising analyzing temporal changes in the current biomechanical signals to characterize the non-fatigue level and the discomfort fatigue level; and wherein setting a training recommendation alters the recommended training target to transition between satisfying the non-fatigue level and the discomfort fatigue level multiple times.

10. The method of claim 1, wherein the suggestion of how the participant should alter his or her activity to manage the fatigue state being endured by the participant comprises generating a map of running route options.

11. The method of claim 1, wherein the suggestion of how the participant should alter his or her activity to manage the fatigue state being endured by the participant comprises an injury warning when the fatigue state is classified as an injury risk fatigue state.

12. The method of claim 1, wherein the fatigue model is a heuristic-based model.

13. The method of claim 1, wherein the fatigue model is a machine intelligence model.

* * * * *